(12) United States Patent
Lee et al.

(10) Patent No.: US 9,932,591 B2
(45) Date of Patent: Apr. 3, 2018

(54) REDUCTION OF LIPASE ACTIVITY IN PRODUCT FORMULATIONS

(71) Applicants: Kelvin Lee, Newark, DE (US); Abraham Lenhoff, Newark, DE (US); Kristin Valente, Plymouth Meeting, PA (US); Nick Levy, Philadelphia, PA (US); Yatin Gokarn, San Diego, CA (US)

(72) Inventors: Kelvin Lee, Newark, DE (US); Abraham Lenhoff, Newark, DE (US); Kristin Valente, Plymouth Meeting, PA (US); Nick Levy, Philadelphia, PA (US); Yatin Gokarn, San Diego, CA (US)

(73) Assignee: University of Delaware, Newark, DE (US)

( * ) Notice: Subject to any disclaimer, the term of this patent is extended or adjusted under 35 U.S.C. 154(b) by 40 days.

(21) Appl. No.: 15/105,925

(22) PCT Filed: Dec. 18, 2014

(86) PCT No.: PCT/US2014/071234
§ 371 (c)(1),
(2) Date: Jun. 17, 2016

(87) PCT Pub. No.: WO2015/095568
PCT Pub. Date: Jun. 25, 2015

(65) Prior Publication Data
US 2016/0312226 A1    Oct. 27, 2016

Related U.S. Application Data

(60) Provisional application No. 61/917,555, filed on Dec. 18, 2013.

(51) Int. Cl.
| | |
|---|---|
| *C12N 15/11* | (2006.01) |
| *C12N 15/113* | (2010.01) |
| *C07K 16/00* | (2006.01) |
| *C12P 21/02* | (2006.01) |
| *C12N 9/20* | (2006.01) |
| *A61K 38/17* | (2006.01) |
| *A61K 38/39* | (2006.01) |
| *A61K 38/42* | (2006.01) |
| *A61K 38/44* | (2006.01) |
| *A61K 38/45* | (2006.01) |
| *A61K 38/48* | (2006.01) |
| *A61K 38/52* | (2006.01) |
| *A61K 47/26* | (2006.01) |
| *C12P 21/00* | (2006.01) |

(52) U.S. Cl.
CPC ...... *C12N 15/1137* (2013.01); *A61K 38/1709* (2013.01); *A61K 38/1741* (2013.01); *A61K 38/1761* (2013.01); *A61K 38/1774* (2013.01); *A61K 38/39* (2013.01); *A61K 38/42* (2013.01); *A61K 38/44* (2013.01); *A61K 38/443* (2013.01); *A61K 38/45* (2013.01); *A61K 38/482* (2013.01); *A61K 38/488* (2013.01); *A61K 38/4813* (2013.01); *A61K 38/52* (2013.01); *A61K 47/26* (2013.01); *C07K 16/00* (2013.01); *C12N 9/20* (2013.01); *C12P 21/005* (2013.01); *C12P 21/02* (2013.01); *C12N 2310/10* (2013.01); *C12N 2310/14* (2013.01); *C12N 2310/20* (2017.05); *C12Y 104/03013* (2013.01); *C12Y 111/01015* (2013.01); *C12Y 205/01018* (2013.01); *C12Y 207/04006* (2013.01); *C12Y 207/11001* (2013.01); *C12Y 301/01034* (2013.01); *C12Y 304/16005* (2013.01); *C12Y 304/21* (2013.01); *C12Y 304/23005* (2013.01); *C12Y 502/01008* (2013.01); *C12Y 503/04001* (2013.01)

(58) Field of Classification Search
None
See application file for complete search history.

(56) References Cited

U.S. PATENT DOCUMENTS 4,603,106 A * 7/1986 Cerami ............... C07K 14/4703
435/18
2012/0328614 A1    12/2012 Burke et al.

FOREIGN PATENT DOCUMENTS

| WO | WO 2004/013280 A2 | 2/2004 |
|---|---|---|
| WO | WO 2008/054514 A2 | 5/2008 |
| WO | WO 2013/013017 A2 | 1/2013 |

OTHER PUBLICATIONS

Augustus et al., Loss of lipoprotein lipase-derived fatty acids leads to increased cardiac glucose metabolism and heart dysfunction, 2006, JBC, vol. 281, pp. 8716-8723.*
Lopez et al., Down-regulation of lipoprotein lipase increases glucose uptake in L6 muscle cells, 2009, BBRC, vol. 389, pp. 34-39.*
Makoveichuk et al., Inactivation of lipoprotein lipase in 3T3-L1 adipocytes by angiopoietin-like protein 4 requires that both proteins have reached the cell surface, 2013, BBRC, vol. 441, pp. 941-946.*
Kuemmerle et al., Lipoprotein lipase links dietary fat to solid tumor cell proliferation, 2011, Molecular Cancer Therapeutics, vol. 10, pp. 427-436.*

(Continued)

*Primary Examiner* — Dana H Shin
(74) *Attorney, Agent, or Firm* — RatnerPrestia

(57) ABSTRACT

The invention relates a method for producing a stable recombinant protein, comprising growing a non-naturally occurring host cell in a culture medium to produce a recombinant protein, and making a composition comprising the recombinant protein and a polysorbate. The production of endogenous lipoprotein lipase by the host cell is reduced. The endogenous lipoprotein lipase is present in the composition in a small amount, and is capable of degrading the polysorbate. The invention also relates to the relevant host cells and compositions, and preparation thereof.

4 Claims, 17 Drawing Sheets

(56) References Cited

OTHER PUBLICATIONS

Christiansen et al., Eur. J. Pharm. Sci., 41:376-82 (2010).
Grzeskowiak et al., Protein Expr. Purif., 66:58-65 (2009).
Hammond and Lee, Biotechnol. Bioeng., 109:528-35 (2009).
Hogwood et al., Biotechnol. Bioeng., 110:240-51 (2013).
Jin et al., Biotechnol. Bioeng., 105:306-16 (2009).
Joucla et al., J Chromatogr., B 942-943:126-33 (2013).
Levy et al., Biotechnol. Bioeng., 111:904-12 (2014).
Mori et al., Biotechnol. Bioeng., 88:901-08 (2004).
Pezzini et al., J. Chromatogr., A 1218:8197-208 (2011).
Tait et al., Biotechnol. Bioeng., 109:971-82 (2011).
Valente et al., Electrophoresis, 33:1947-57 (2012).
Valente et al., Biotechnol. J., 9:87-99 (2014).
Khossravi et al., Pharmaceutical Research, 19(5):634-39 (2002).
PCT/US2014/071234 International Search Report dated Apr. 20, 2015 by Blaine R. Copenheaver.

\* cited by examiner

FIGURES 1A-D
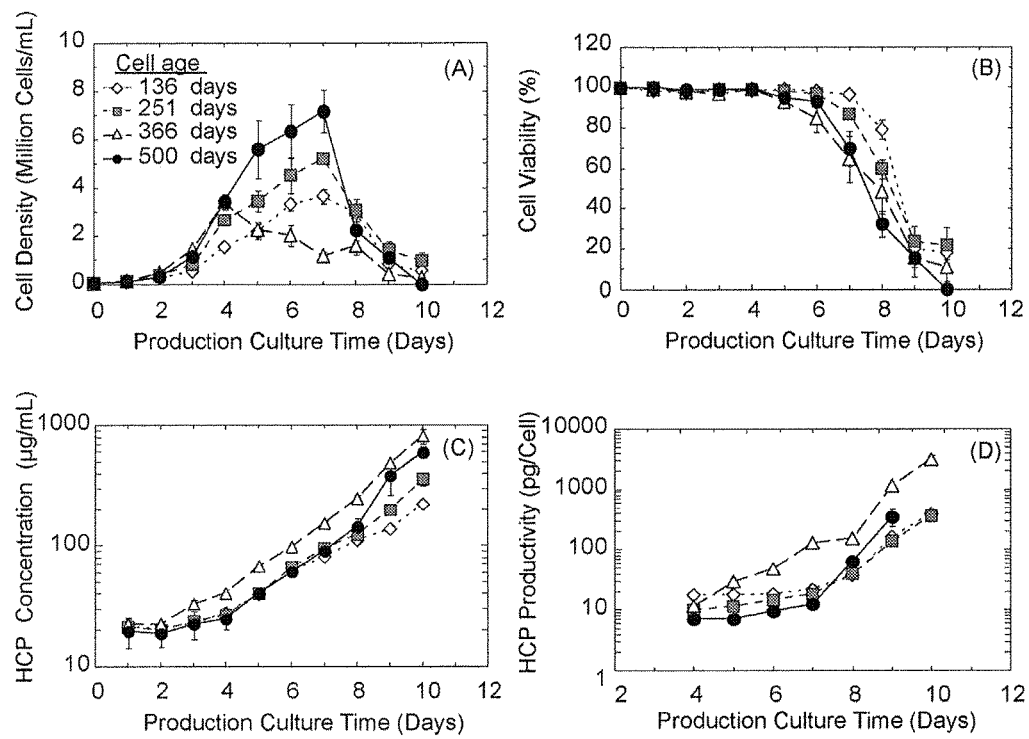

FIGURES 2A-B

Relative Protein Expression by Shotgun Proteomics

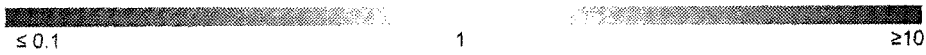

≤ 0.1    1    ≥10

(A) 24 CHO HCPs with cell age-dependent expression by shotgun proteomics

| Trend | Max p-value vs. day 136 | Cell age (days) 136 | 251 | 366 | 500 | Protein Name |
|---|---|---|---|---|---|---|
| Minimum at 136 days | <1.0·10$^{-15}$ | | | | | Laminin subunit alpha-5 |
| | 1.3·10$^{-15}$ | | | | | Laminin subunit beta-1 |
| | 7.2·10$^{-12}$ | | | | | Laminin subunit gamma-1 |
| | 3.6·10$^{-6}$ | | | | | Nidogen-1 |
| | 1.7·10$^{-3}$ | | | | | Latent TGF-beta complexed protein (LTCP) |
| | 1.9·10$^{-3}$ | | | | | Insulin-like growth factor-binding protein 4 |
| | 2.2·10$^{-3}$ | | | | | Metalloproteinase inhibitor 1 |
| | 1.9·10$^{-3}$ | | | | | Lactadherin |
| Maximum at 136 days | <1.0·10$^{-15}$ | | | | | Basement membrane-specific heparan sulfate proteoglycan core protein |
| | 8.9·10$^{-13}$ | | | | | Chondroitin sulfate proteoglycan 4 |
| | 3.2·10$^{-6}$ | | | | | Phospholipid transfer protein |
| | 1.0·10$^{-3}$ | | | | | Galectin-3-binding protein |
| | 8.7·10$^{-4}$ | | | | | Extracellular matrix protein 1 |
| | 2.1·10$^{-3}$ | | | | | G-protein coupled receptor 56[a] |
| | 1.1·10$^{-3}$ | | | | | Cathepsin D[a] |
| | 2.6·10$^{-3}$ | | | | | Granulins[a] |
| Max. at 136 days and min. at 366 days | 8.6·10$^{-7}$ | | | | | Fibronectin[a] |
| | 2.6·10$^{-6}$ | | | | | Lysosomal protective protein |
| | 7.2·10$^{-4}$ | | | | | Putative phospholipase B-like 2 |
| | 1.1·10$^{-3}$ | | | | | Thrombospondin-3[a] |
| | 3.1·10$^{-3}$ | | | | | Retinoid-inducible serine carboxypeptidase[a] |
| | 4.4·10$^{-3}$ | | | | | Beta-galactosidase |
| | 5.2·10$^{-3}$ | | | | | Acid ceramidase |
| | 7.0·10$^{-3}$ | | | | | Legumain |

Relative Protein Expression by Shotgun Proteomics

≤ 0.1    1    ≥10

(B) 20 CHO HCPs with HCP productivity-dependent expression by shotgun proteomics

| Trend | Max p-value vs. day 366 | Productivity (pg/cell) [Cell age (days)] 10 [500] | 12 [251] | 19 [136] | 26 [366] | Protein Name |
|---|---|---|---|---|---|---|
| Minimum at 366 days | 1.1·10$^{-15}$ | | | | | Complement C3 |
| | 9.1·10$^{-9}$ | | | | | Matrix metalloproteinase-9 |
| | 1.1·10$^{-6}$ | | | | | Complement C1r-A subcomponent |
| | 1.1·10$^{-5}$ | | | | | Beta-glucuronidase |
| | 3.7·10$^{-3}$ | | | | | Beta 2-microglobulin |
| | 2.8·10$^{-4}$ | | | | | Calcium-dependent serine proteinase |
| | 1.4·10$^{-3}$ | | | | | Neural cell adhesion molecule 1 |
| | 1.8·10$^{-7}$ | | | | | EMILIN-1 |
| | 5.4·10$^{-5}$ | | | | | Peptidyl-prolyl cis-trans isomerase B[b] |
| | 8.2·10$^{-4}$ | | | | | C-C motif chemokine 2[b] |
| | 9.9·10$^{-4}$ | | | | | N(4)-(beta-N-acetylglucosaminyl)-L-asparaginase[b] |
| Maximum at 366 days | <1.0·10$^{-15}$ | | | | | 78 kDa glucose-regulated protein |
| | 6.4·10$^{-5}$ | | | | | Thrombospondin-1 |
| | 2.9·10$^{-3}$ | | | | | Semaphorin-3E |
| | 2.1·10$^{-3}$ | | | | | Glucosidase 2 subunit beta |
| | 6.1·10$^{-3}$ | | | | | Hypoxia up-regulated protein 1 |
| | 3.5·10$^{-3}$ | | | | | Neutral alpha-glucosidase AB |
| | 6.5·10$^{-3}$ | | | | | Endoplasmin |
| | 8.3·10$^{-3}$ | | | | | Plasminogen activator inhibitor 1 |
| | 9.0·10$^{-3}$ | | | | | Inter-alpha-trypsin inhibitor heavy chain H5 |

FIGURES 3A-B
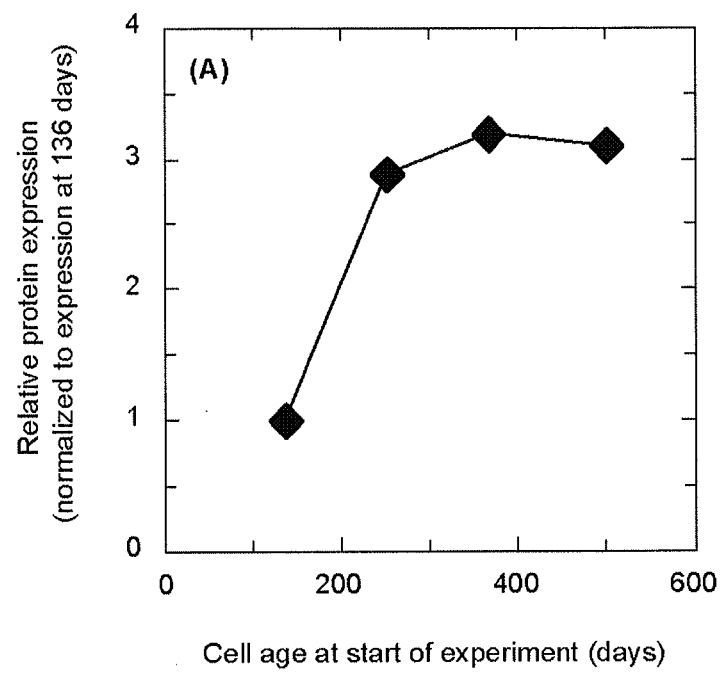
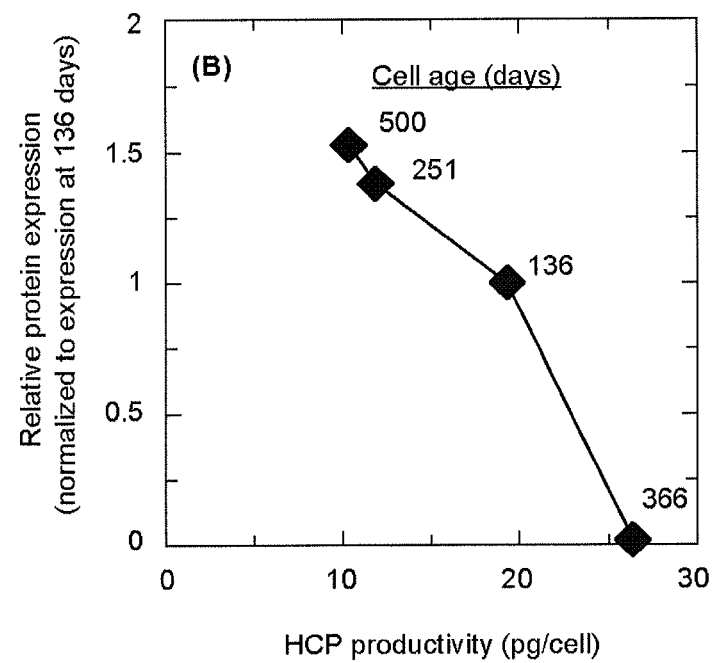

FIGURES 4A-D
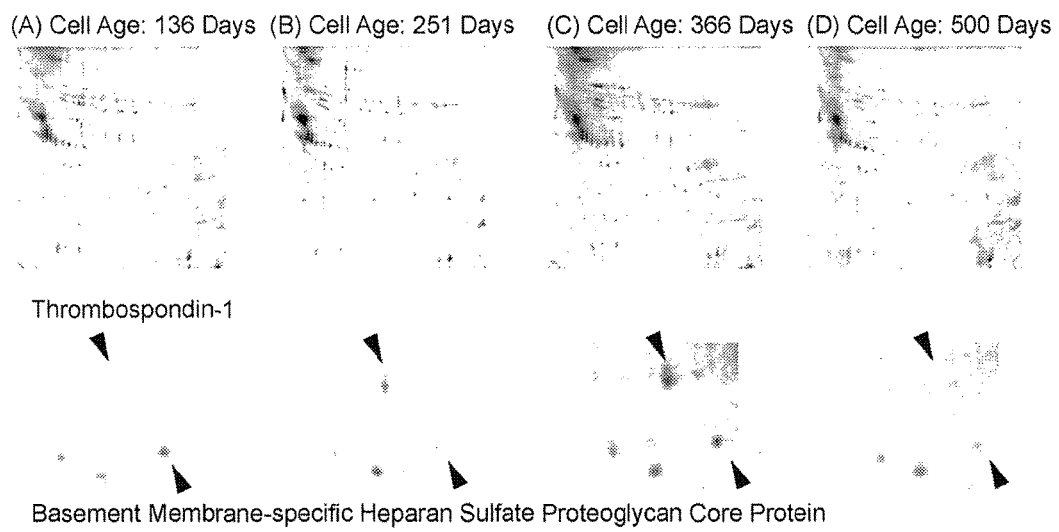

FIGURES 10A-B
A.
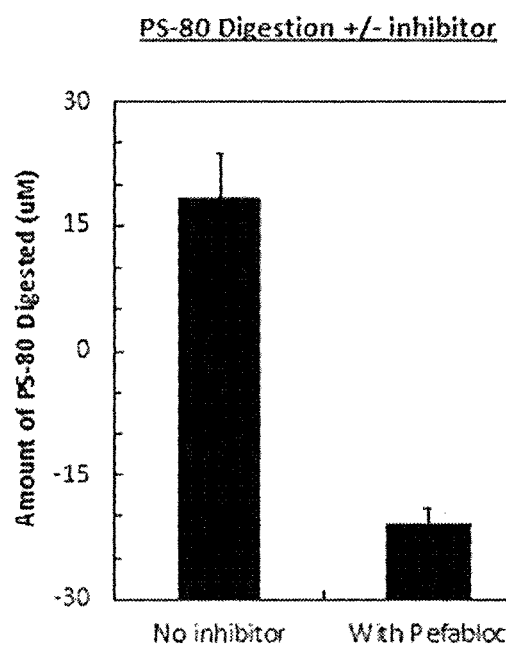
B.
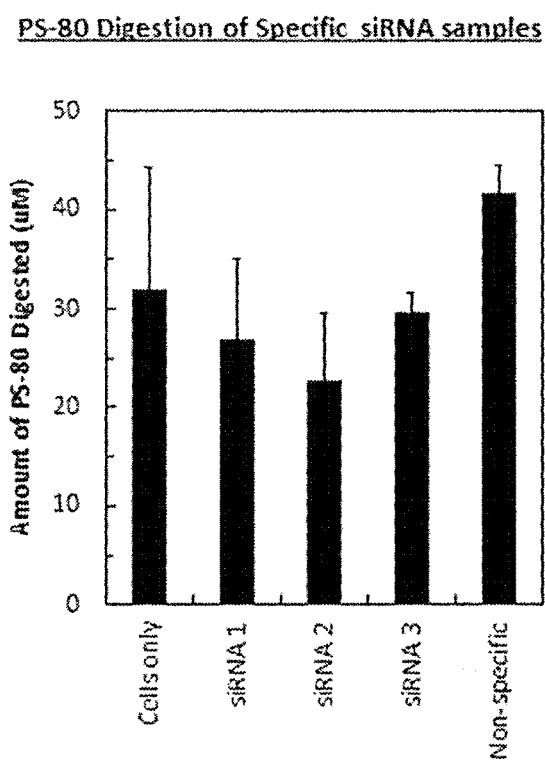

FIGURES 13A-B

SEQUENCE LISTING

<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
gcaacaaugu gggcuaugat t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
ucauagccca cauuguugct t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3 ccuucuccu gaugaugcat t                                               21

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
ugcaucauca ggagaaaggt t                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
gaaaugaugu ggccagguut t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
aaccuggcca caucauuuct t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic

```
<400> SEQUENCE: 7 cuugucauc gagaagauut t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
aaucuucucg augacaaagt t                                             21

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gaaguauugg gauccagaat t                                             21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
uucuggaucc caauacuuct t                                             21

<210> SEQ ID NO 11
<211> LENGTH: 19
<212> TYPE: DNA
<213> ORGANISM: Cricetulus griseus

<400> SEQUENCE: 11
gcaacaatgt gggctatga                                                19

<210> SEQ ID NO 12
<211> LENGTH: 19
<212> TYPE: DNA
<213> ORGANISM: Cricetulus griseus

<400> SEQUENCE: 12
tcatagccca cattgttgc                                                19

<210> SEQ ID NO 13
<211> LENGTH: 19
<212> TYPE: DNA
<213> ORGANISM: Cricetulus griseus

<400> SEQUENCE: 13
cctttctcct gatgatgca                                                19

<210> SEQ ID NO 14
<211> LENGTH: 19
<212> TYPE: DNA
<213> ORGANISM: Cricetulus griseus

<400> SEQUENCE: 14
```

```
tgcatcatca ggagaaagg                                                19
```

```
<210> SEQ ID NO 15
<211> LENGTH: 19
<212> TYPE: DNA
<213> ORGANISM: Cricetulus griseus

<400> SEQUENCE: 15
gaaatgatgt ggccaggtt                                                19

<210> SEQ ID NO 16
<211> LENGTH: 19
<212> TYPE: DNA
<213> ORGANISM: Cricetulus griseus

<400> SEQUENCE: 16
aacctggcca catcatttc                                                19

<210> SEQ ID NO 17
<211> LENGTH: 19
<212> TYPE: DNA
<213> ORGANISM: Cricetulus griseus

<400> SEQUENCE: 17
ctttgtcatc gagaagatt                                                19

<210> SEQ ID NO 18
<211> LENGTH: 19
<212> TYPE: DNA
<213> ORGANISM: Cricetulus griseus

<400> SEQUENCE: 18
aatcttctcg atgacaaag                                                19

<210> SEQ ID NO 19
<211> LENGTH: 19
<212> TYPE: DNA
<213> ORGANISM: Cricetulus griseus

<400> SEQUENCE: 19
gaagtattgg gatccagaa                                                19

<210> SEQ ID NO 20
<211> LENGTH: 19
<212> TYPE: DNA
<213> ORGANISM: Cricetulus griseus

<400> SEQUENCE: 20
ttctggatcc caatacttc                                                19

<210> SEQ ID NO 21
<211> LENGTH: 19
<212> TYPE: PRT
<213> ORGANISM: Cricetulus griseus

<400> SEQUENCE: 21

Ile Thr Gly Leu Asp Pro Ala Gly Pro Asn Phe Glu Tyr Ala Glu Ala
1               5                   10                  15

Pro Ser Arg

<210> SEQ ID NO 22
<211> LENGTH: 14
<212> TYPE: PRT
```

-continued

<213> ORGANISM: Cricetulus griseus

<400> SEQUENCE: 22

Glu Pro Asp Ser Asn Val Ile Val Val Asp Trp Leu Tyr Arg
1               5                   10

<210> SEQ ID NO 23
<211> LENGTH: 17
<212> TYPE: PRT
<213> ORGANISM: Cricetulus griseus

<400> SEQUENCE: 23

Leu Ser Pro Asp Asp Ala Asp Phe Val Asp Val Leu His Thr Phe Thr
1               5                   10                  15
Arg

<210> SEQ ID NO 24
<211> LENGTH: 10
<212> TYPE: PRT
<213> ORGANISM: Cricetulus griseus

<400> SEQUENCE: 24

Gly Leu Gly Asp Val Asp Gln Leu Val Lys
1               5                   10

<210> SEQ ID NO 25
<211> LENGTH: 9
<212> TYPE: PRT
<213> ORGANISM: Cricetulus griseus

<400> SEQUENCE: 25

Ala Asn Glu Leu Leu Ile Asn Val Lys
1               5

<210> SEQ ID NO 26
<211> LENGTH: 15
<212> TYPE: PRT
<213> ORGANISM: Cricetulus griseus

<400> SEQUENCE: 26

Ala Asn Gly Thr Thr Val Leu Val Gly Met Pro Ala Gly Ala Lys
1               5                   10                  15

<210> SEQ ID NO 27
<211> LENGTH: 8
<212> TYPE: PRT
<213> ORGANISM: Cricetulus griseus

<400> SEQUENCE: 27

Glu Ala Leu Asp Phe Phe Ala Arg
1               5

<210> SEQ ID NO 28
<211> LENGTH: 13
<212> TYPE: PRT
<213> ORGANISM: Cricetulus griseus

<400> SEQUENCE: 28

Val Val Gly Leu Ser Thr Leu Pro Glu Ile Tyr Glu Lys
1               5                   10

REDUCTION OF LIPASE ACTIVITY IN PRODUCT FORMULATIONS

CROSS-REFERENCE TO RELATED APPLICATION

This application is a U.S. national phase application of International Application No. PCT/US2014/071234, filed Dec. 18, 2014, claiming the benefit of U.S. Provisional Application No. 61/917,555, filed Dec. 18, 2013, the contents of each of which are incorporated herein in their entireties for all purposes.

REFERENCE TO U.S. GOVERNMENT SUPPORT

This work is supported by a grant from the National Science Foundation (NSF) (Award No. CBET-0966644). The United States has certain rights in the invention.

FIELD OF THE INVENTION

The invention relates generally to making formulations of stable recombinant proteins produced by non-naturally occurring host cells.

BACKGROUND OF THE INVENTION

Chinese hamster ovary (CHO) cells are integral to the $125 billion biopharmaceutical market, which includes monoclonal antibodies (mAbs) and other therapeutic proteins. Recent sequencing of the Chinese hamster and Chinese hamster ovary (CHO) cell genomes enables cell engineering strategies to address a wide variety of problems encountered in biopharmaceutical manufacturing. One particular application involves studies of CHO host cell proteins (HCPs) that may be difficult to remove for a variety of reasons. The presence of HCPs is regulated for patient safety concerns but may also have an impact on product quality in the context of formulation.

Polysorbates are a class of non-ionic surfactants that are added to biopharmaceutical formulations to improve the stability of therapeutic proteins by limiting aggregation and surface adsorption. Monoclonal antibody formulations often incorporate a polysorbate such as polysorbate 80 (PS-80) and polysorbate 20 (PS-20) to prolong the shelf-life of drug products. Polysorbate degradation over time can impact the stability of those drug products.

There remains a need for improved mammalian host cells for producing stable recombinant proteins by, for example, mitigating polysorbate degradation.

SUMMARY OF THE INVENTION

The present invention relates to host cells suitable for producing a stable recombinant protein, compositions comprising the stable recombinant proteins, methods for producing the stable recombinant proteins by the host cells, and methods for preparing the host cells and the compositions.

According to a first aspect of the present invention, a non-naturally occurring host cell for producing a stable recombinant protein is provided. The production of endogenous lipase, for example, lipoprotein lipase (LPL), by the host cell is reduced. Preferably, the lipase is LPL. The production of the endogenous lipase (e.g., LPL) may be reduced by at least about 10%, 20%, 30%, 40%, 60%, 70%, 80%, 90% or 95%. No more than about 1%, 5%, 10%, 20%, 30%, 40%, 60%, 70%, 80%, 90% or 95% of the recombinant protein may be bound to the endogenous lipase (e.g., LPL).

The host cell may be a mammalian cell selected from the group consisting of CHO, 3T3, BHK, HeLa, NS0, HepG2, and derivatives thereof. Preferably, the host cell is a CHO cell.

The host cell may express an interfering RNA specific for the endogenous lipase (e.g., LPL). The interfering RNA may be selected from the group consisting of small interfering RNAs (siRNAs), short hairpin RNAs (shRNAs), and bifunctional RNAs. The interfering RNA may be encoded by the genome of the host cell.

At least one copy of an endogenous gene encoding the endogenous lipase (e.g., LPL) may be knocked out from the genome of the host cell. Preferably, all copies of the endogenous gene are knocked out.

According to a second aspect of the invention, a composition is provided. The composition comprises a stable recombinant protein and a polysorbate. The recombinant protein is produced by a non-naturally occurring host cell. The production of endogenous lipase (e.g., LPL) by the host cell is reduced. The endogenous lipase (e.g., LPL) is present in the composition in a small amount (e.g., less than about 10%, 5%, 1%, 0.1%, 0.01%, 0.001% or 0.0001% by weight), and is capable of degrading the polysorbate.

The composition may further comprise an inhibitor of the endogenous lipase (e.g., LPL). The inhibitor may inhibit the lipase (e.g., LPL) from binding the recombinant protein. The inhibitor may inhibit the lipase from degrading the polysorbate.

At least about 10%, 20%, 30%, 40%, 60%, 70%, 80%, 90% or 95% of the recombinant protein in the composition may remain over a predetermined period of time, for example, 1 day, 1 week, 2 weeks, 1 month, 3 months, 6 months or 1 year.

Where the recombinant protein has a biological activity, at least about 10%, 20%, 30%, 40%, 60%, 70%, 80%, 90% or 95% of the biological activity remains over a predetermined period of time, for example, 1 day, 1 week, 2 weeks, 1 month, 3 months, 6 months or 1 year.

The recombinant protein may be an antibody, preferably a monoclonal antibody, more preferably a humanized antibody.

The polysorbate may comprise polysorbate 80, polysorbate 20, polysorbate 40, polysorbate 60, polysorbate 65, or a combination thereof.

According to a third aspect of the invention, a method for producing a stable recombinant protein is provided. The method comprises (a) growing a non-naturally occurring host cell in a culture medium to produce the recombinant protein, and (b) making a composition comprising the recombinant protein and a polysorbate. The production of endogenous lipase (e.g., LPL) by the host cell is reduced. The endogenous lipase (e.g., LPL) is present in the composition in a small amount (e.g., less than about 10%, 5%, 1%, 0.1%, 0.01%, 0.001% or 0.0001% by weight), and is capable of degrading the polysorbate. The recombinant protein in the composition is stable.

According to the production method, the polysorbate may comprise polysorbate 80, polysorbate 20, polysorbate 40, polysorbate 60, polysorbate 65, or a combination thereof. The production of the endogenous lipase (e.g., LPL) by the host cell may be reduced by at least about 10%, 20%, 30%, 40%, 60%, 70%, 80%, 90% or 95%.

According to the production method, at least about 95%, 90%, 80%, 70%, 60%, 50%, 40%, 30%, 20% or 10% of the stable recombinant protein may remain over a predetermined period of time, for example, 1 day, 1 week, 2 weeks, 1 month, 3 months, 6 months or 1 year. Where the stable recombinant protein is biologically active, at least about 95%, 90%, 80%, 70%, 60%, 50%, 40%, 30%, 20% or 10% of the biological activity may remain over a predetermined period of time, for example, 1 day, 1 week, 2 weeks, 1 month, 3 months, 6 months or 1 year. The recombinant protein may be an antibody, preferably a monoclonal antibody, more preferably a humanized antibody.

According to the production method, the host cell may be a mammalian cell selected from the group consisting of CHO, 3T3, BHK, HeLa, NS0, HepG2, and derivatives thereof. Preferably, the host cell is a CHO cell.

The production method may further comprise expressing an interfering RNA specific for the lipase (e.g., LPL) in the host cell. The interfering RNA may be selected from the group consisting of small interfering RNAs (siRNAs), short hairpin RNAs (shRNAs), and bifunctional RNAs. The interfering RNA may be encoded by the genome of the host cell.

The production method may further comprise knocking out at least one copy of an endogenous gene encoding the endogenous lipase (e.g., LPL) from the genome of the host cell. Preferably, all copies of the endogenous gene encoding the endogenous lipase (e.g., LPL) are knocked out from the genome of the host cell.

The production method may further comprise removing the endogenous lipase (e.g., LPL) from the composition.

The production method may further comprise adding an inhibitor of the endogenous lipase (e.g., LPL) to the composition. The inhibitor may inhibit the lipase (e.g., LPL) from binding the recombinant protein. The inhibitor may inhibit the lipase from degrading the polysorbate.

According to a fourth aspect of the invention, a method for preparing a non-naturally occurring host cell suitable for producing a recombinant protein is provided. The preparation method comprises reducing the production of endogenous lipase (e.g., LPL) by the host cell.

The preparation method may further comprise expressing an interfering RNA specific for the lipase (e.g., LPL) in the host cell. The interfering RNA may be selected from the group consisting of small interfering RNAs (siRNAs), short hairpin RNAs (shRNAs), and bifunctional RNAs. The interfering RNA may be encoded by the genome of the host cell.

The preparation method may further comprise knocking out at least one copy, preferably all copies, of an endogenous gene encoding the endogenous lipase (e.g., LPL) from the genome of the host cell. The host cell may be a mammalian cell selected from the group consisting of CHO, 3T3, BHK, HeLa, NS0, HepG2, and derivatives thereof. Preferably, the host cell is a CHO cell.

According to a fifth aspect of the invention, a method for preparing a composition comprising a recombinant protein and a polysorbate is provided. The preparation method comprises adding a polysorbate to a formulation comprising a recombinant protein produced by a non-naturally occurring host cell. The preparation method may further comprise adding an inhibitor of the endogenous lipase (e.g., LPL) to the composition. The production of endogenous lipase (e.g., LPL) by the host cell is reduced. The endogenous lipase (e.g., LPL) is present in the composition in a small amount (e.g., less than about 10%, 5%, 1%, 0.1%, 0.01%, 0.001% or 0.0001% by weight), and is capable of degrading the polysorbate. The recombinant protein is stable in the composition.

BRIEF DESCRIPTION OF THE DRAWINGS

FIGS. 1A-D show (A) cell density, (B) cell viability, (C) extracellular HCP concentration, and (D) extracellular HCP productivity per cell over 10 days for CHO cultures aged 136-500 days at the start of the experiment. Error bars represent the standard error of the mean from four biological replicates of production culture sourced from a single cryopreserved stock for each cell age. HCP productivity is unavailable for cells aged 500 days at day 10 of the experiment, as no viable cells remained in culture.

FIGS. 2A-B show heat map of extracellular CHO HCPs demonstrating statistically significant varied expression by shotgun proteomics relative to expression in cells aged 136 days (yellow) with respect to (A) cell age and (B) CHO HCP productivity. Proteins exhibiting increased expression are shown in green, while those with decreased expression are shown in red. Color graduations are based on a logarithmic scale. Statistically indistinguishable pairwise comparisons denoted as $^a$equivalent between 136 and 251 days, and $^b$equivalent between 19 and 26 pg/cell (136 and 366 days).

FIGS. 3A-B show relative expression of (A) laminin subunit α-5 as an example of cell age-dependent expression and (B) complement C3 as an example of HCP productivity-dependent expression.

FIGS. 4A-D show representative 2DE images of extracellular CHO HCPs collected from day five of production culture from cells cultured for (A) 136, (B) 251, (C) 366, and (D) 500 days. Selected spots are magnified to illustrate varied expression.

FIGS. 10A-B show PS-80 digestion (A) depicts the amount of PS-80 digested from a sample with no enzyme inhibitor and shows a high level of PS-80 degradation compared to a sample where an inhibitor (Pefabloc) of LPL is added that significantly reduces the amount of PS-80 degraded (B) shows that the amount of PS-80 degraded by samples derived from CHO cells expressing an siRNA against LPL show a somewhat reduced amount of PS-80 degradation compared to a cell only or a nonspecific control sample.

DETAILED DESCRIPTION OF THE INVENTION

Figure 5:
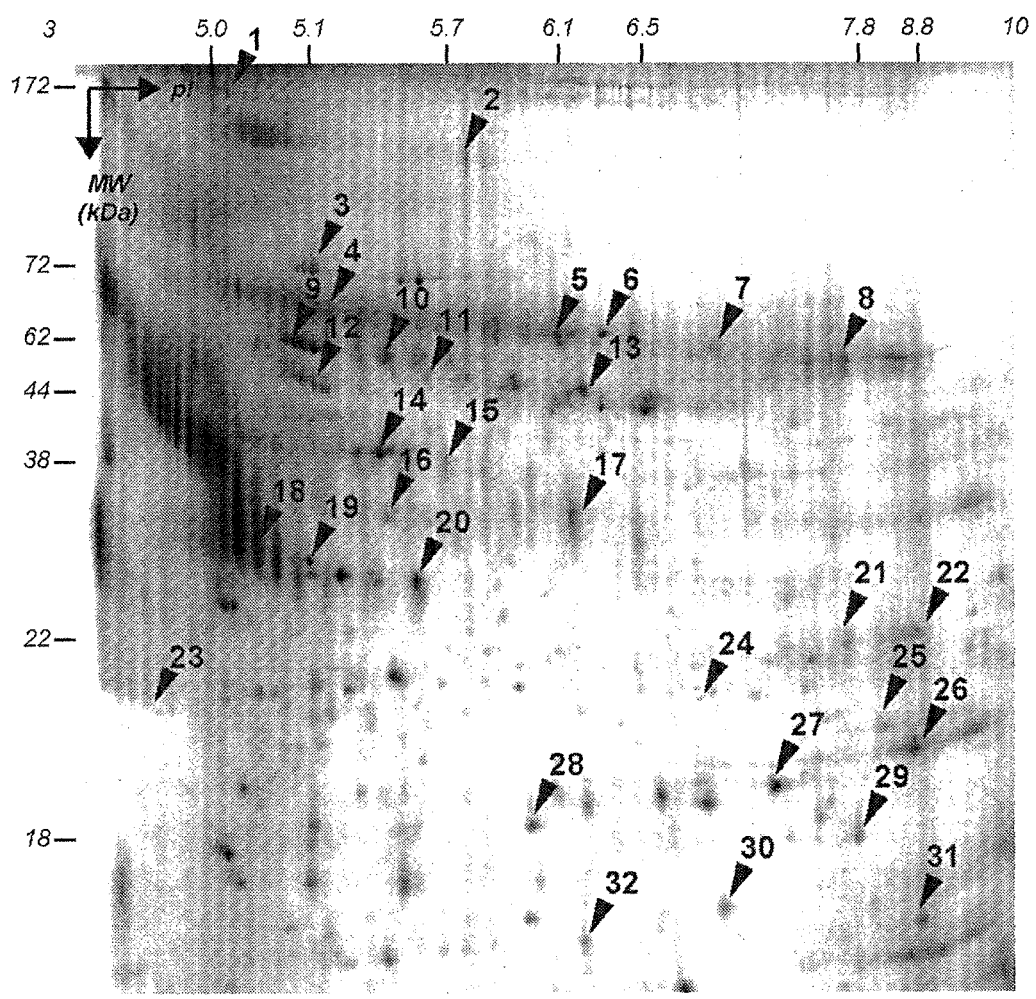
FIG. 5 shows a representative 2DE image of kotein spots that exhibited at least three-fold change in spot volume and were excised and identified by MS. Only one spot is labeled for each protein. Molecular weight (MW) and isoelectric point (pI) labels approximated from the locations of seven identified proteins.

The present invention is based on the discovery that lipoprotein lipase (LPL) is an endogenous CHO host cell protein (HCP) that co-purifies with different monoclonal antibodies produced by CHO host cells and has an enzymatic activity that degrades polysorbate 80 (PS-80) and polysorbate 20 (PS-20). In particular, the present invention relates to mitigating expression of endogenous lipase (e.g., LPL) by mammalian host cells (e.g., CHO cells) to improve stability of recombinant proteins produced by the host cells. There may be two general approaches to reducing or eliminating lipase (e.g., LPL) from a final drug product: reducing or eliminating lipase (e.g., LPL) that appears in an original host cell through a cell engineering approach, or adjusting purification strategies to specifically target lipase (e.g., LPL) removal. One may also add an inhibitor of the lipase (e.g., LPL) in a composition comprising a recombinant protein and a polysorbate.

The terms "protein" and "polypeptide" are used herein interchangeably, and refer to a polymer of amino acid residues with no limitation with respect to the minimum length of the polymer. Preferably, the protein or polypeptide has at least 20 amino acids. The definition includes both full-length proteins and fragments thereof, as well as modifications thereof (e.g., glycosylation, phosphorylation, deletions, additions and substitutions).

The term "polynucleotide" used herein refers to a polymer of nucleotide residues with no limitation with respect to the minimum length of the polymer. Preferably, the polynucleotide has at least 60 nucleotides. The polynucleotide may be a DNA, cDNA or RNA molecule.

The term "variant" of a protein or polynucleotide used herein refers to a polypeptide having an amino acid or a polynucleotide having a nucleic acid sequence that is the same as the amino acid or nucleic acid sequence of the corresponding protein or polynucleotide except having at least one amino acid or nucleic acid modified, for example, deleted, inserted, or replaced, respectively. A variant of a protein or polynucleotide may have an amino acid or nucleic acid sequence at least about 80%, 90%, 95%, or 99%, preferably at least about 90%, more preferably at least about 95%, identical to the amino acid sequence or nucleic acid of the protein or polynucleotide.

The term "lipase" used herein refers to a lipase gene family. Examples include lipoprotein lipase (LPL), pancreatic lipase, hepatic lipase, and endothelial lipase.

Lipoprotein lipase (LPL) is a water soluble enzyme that hydrolyzes triglycerides in lipoproteins, such as those found in chylomicrons and very low-density lipoproteins (VLDL), into two free fatty acids and one monoacylglycerol molecule. It is also involved in promoting the cellular uptake of chylomicron remnants, cholesterol-rich lipoproteins, and free fatty acids.

The term "lipoprotein lipase (LPL)" used herein refers to a full length LPL protein, or a functional fragment or variant thereof. LPL protein sequences and gene sequences in various species (e.g., human, mouse, rat and Chinese hamster) are known in the art. The actual or predicted LPL mRNA sequences of human, mouse, rat and Chinese hamster LPL can be found in the GenBank database Accession Nos. NP_000228, NP_032535, NP_036730, and XP_007607328, respectively. A functional fragment or variant of endogenous LPL produced by a host cell is capable of co-purifying with a recombinant protein, for example, a therapeutic protein, produced by the host cell, and is capable of degrading a polysorbate.

The present invention provides a non-naturally occurring host cell suitable for producing a recombinant protein. The production of endogenous lipase by the host cell is reduced. The lipase is preferably lipoprotein lipase (LPL).

The recombinant protein may be bound to the endogenous lipase (e.g., LPL). In some embodiments, no more than about 1%, 5%, 10%, 20%, 30%, 40%, 60%, 70%, 80%, 90% or 95% the recombinant protein is bound to the endogenous lipase (e.g., LPL).

The term "production" used herein refers expression and secretion of a protein by a host cell. The production of endogenous lipase (e.g., LPL) by a host cell may be reduced by at least about 10%, 20%, 30%, 40%, 60%, 70%, 80%, 90% or 95%, preferably by at least about 20%, more preferably by at least about 50%, most preferably by at least about 95%. In a preferred embodiment, the host cell produces no lipoprotein lipase.

The host cell may be a mammalian cell, preferably a mammalian cell suitable for producing a recombinant protein. The host cell may be selected from the group consisting of 3T3, CHO, BHK, HeLa, HepG2 and NS0 cells, and derivatives of these cells. Preferably, the host cell is a CHO cell. The host cell may be adherent or in suspension, preferably in suspension.

The production of the lipase (e.g., LPL) may be reduced by various methods known in the art. For example, the expression of the lipase (e.g., LPL) in host cells (e.g., CHO cells) may be reduced by using an interfering RNA approach to reduce the amount of the lipase (e.g., LPL) transcript expression or by eliminating the lipase (e.g., LPL) gene from the genome of host cells (e.g., CHO cells) using a genome editing method.

The host cell may express an interfering RNA specific for the lipase (e.g., LPL). The interfering RNA is capable of interfering with the expression of an endogenous gene encoding the lipase (e.g., LPL) and causing reduced production of the lipase (e.g., LPL) by a host cell comprising the interfering RNA when compared with that by a control cell. The control cell is the same as the host cell except that its endogenous lipase (e.g., LPL) production is not altered. The control cell may be a naturally occurring cell. The interfering RNA may be selected from the group consisting of small interfering RNAs (siRNAs), short hairpin RNAs (shRNAs), and bifunctional RNAs.

Conventional RNA interference (RNAi) design and construction techniques may be used to make an interfering RNA specific for the lipase (e.g., LPL) by targeting any segment of a lipase (e.g., LPL) mRNA. For example, an siRNA sequence may be complementary with a segment of a lipase (e.g., LPL) mRNA sequence in a host cell. Where the lipase (e.g., LPL) mRNA sequence is not known in a host cell, a lipase (e.g., LPL) cDNA may be obtained from the host cell using conventional techniques known in the art. For example, a lipase (e.g., LPL) cDNA may be isolated from a host cell and sequenced to define target regions for gene silencing based on previously published siRNA design guidelines. Various sequence segments, preferably conserved regions within the lipase (e.g., LPL) cDNA sequence among different species may be selected. For example, a LPL-specific siRNA sequence may target an LPL mRNA segment sequence corresponding to an LPL gene sequence (XM_003499928.1) as set forth in Table 1. siRNA duplexes may be synthesized, and screened for silencing efficiency in host cells, for example, CHO cells.

A lipase (e.g., LPL) specific interfering RNA may be introduced into a host cell by various transfection methods. An effective lipase (e.g., LPL) specific interfering RNA may be introduced in a host cell for stable expression using techniques known in the art, for example, via shRNA vectors. The host cell may express the lipase (e.g., LPL) specific interfering RNA transiently or stably, preferably stably. The lipase (e.g., LPL) specific interfering RNA may be encoded by the genome of the host cell.

The production of endogenous lipase (e.g., LPL) by a host cell may also be accomplished by knocking out at least one copy of an endogenous gene encoding the endogenous lipase (e.g., LPL) from the genome of the host cell. In a preferred embodiment, all copies of the endogenous lipase (e.g., LPL) gene are knocked out from the genome of the host cell, and the lipase (e.g., LPL) production is eliminated. Exemplary genome editing methods include CRISPR/Cas9 and TAL-ENs.

Successful reduction or elimination of endogenous lipase (e.g., LPL) may be monitored using various techniques known in the art or customized for this purpose. For example, production of endogenous lipase (e.g., LPL) by host cells may be reflected by degradation of PS-80 in a fatty acid assay using samples derived from the host cells. The degradation specificity by the lipase (e.g., LPL) may be determined by using an inhibitor such as Pefabloc.

The host cell may further comprise a nucleic acid sequence encoding a recombinant protein. The nucleic acid sequence encoding a recombinant protein may be integrated into the genome of the host cell. The host cell may produce the recombinant protein, either transient or stably, preferably stably.

The present invention also provides a composition comprising a stable recombinant protein and a polysorbate. The recombinant protein is produced by the non-naturally occurring host cell of the present invention. The endogenous lipase (e.g., LPL) is present in the composition in a small amount (e.g., less than about 10%, 5%, 1%, 0.1%, 0.01%, 0.001% or 0.0001%, preferably less than about 0.1%, by weight). The endogenous lipase (e.g., LPL) is capable of degrading the polysorbate. Preferably, the composition comprises no lipase (e.g., LPL).

The recombinant protein in the composition is stable. For example, at least about 10%, 20%, 30%, 40%, 60%, 70%, 80%, 90% or 95%, preferably at least about 90%, more preferably at least about 95%, most preferably 100%, of the recombinant protein remains over a predetermined period of time, for example, about 1 day, 1 week, 2 weeks, 1 month, 3 months, 6 months or 1 year, preferably about 3 months.

The recombinant protein may be a biopharmaceutical protein. It may be an antibody, preferably a monoclonal antibody, more preferably a humanized antibody. Exemplary recombinant proteins include monoclonal antibodies (e.g., anti-EGFR mAb, anti-VEGF mAb, anti-Factor VIII mAb, anti-IgE mAb, anti-CD11a mAb, anti-interferon-β mAb, anti-TNFα mAb, anti-CD52mAb, anti-HER2mAb, and anti-CD20 mAb), human secreted alkaline phosphatase (SEAP), tissue plasminogen activator (tPA), α-glucosidase, laronidase, Ig-CTLA4 fusion, N-acetylgalactosamine-4-sulfatase, luteinizing hormone, erythropoietin, TNFα receptor fusion, Factor IX, follicle stimulating hormone, β-glucocerebrosidase, and deoxyribonuclease I. The recombinant proteins may have various targets and mechanisms of action, for example, Alpha4/beta1/7 integrin, Alpha-galactosidase ERT, ATIII substitution, B-lymphocyte stimulator (BLyS), CD20, Complement C5 antagonist, EGF-R, EpCAM (cancer target) and CD3 (T cell recruitment), Epitope on RS virus, Factor VIII substitution, G-CSF receptor, Glycoprotein IIb/IIIa antagonist, Growth hormone (GH) receptor antagonist, hGH receptor, Human gluco-cerebrosidase ERT, Iduronate-2-sulfatase enzyme replacement, IL-1 beta antagonist, IL-12 (p40) and IL-23, Insulin receptor, Insulin-like growth factor-1 (IGF-1) receptor agonist, Interferon alpha receptor, Interleukin-1 receptor (IL-1R) antagonist, Kallikrein, Keratinocyte growth factor receptor, Neuromus-cular transmission (SNAP-25 cleavage), Substitution of coagulation Factor VIIa, Thrombopoietin (TPO) receptor agonist, TNF alpha antagonist, TNF-alpha (soluble and membrane bound), and Vascular endothelial growth factor (VEGF).

Where the recombinant protein has a biological activity, for example, a therapeutic effect, at least about 10%, 20%, 30%, 40%, 60%, 70%, 80%, 90% or 95%, preferably at least about 90%, more preferably at least about 95%, most preferably 100%, of the biological activity remains over a predetermined period of time, for example, about 1 day, 1 week, 2 weeks, 1 month, 3 months, 6 months or 1 year, preferably about 3 months.

The polysorbate may be present at about 0.001-1%, preferably 0.01-0.02% % by weight in the composition of the present invention. The polysorbate may be composed of one or more polyoxyethylene sorbitan monooleate fatty acid esters. For example, the polysorbate may comprise polysorbate 80, polysorbate 20, polysorbate 40, polysorbate 60, polysorbate 65, or a combination thereof.

In the composition, the recombinant protein may be bound to the endogenous lipase (e.g., LPL) produced by the same host cell. In some embodiments, no more than about 1%, 5%, 10%, 20%, 30%, 40%, 60%, 70%, 80%, 90% or 95% of the recombinant protein in the composition is bound to the endogenous lipase (e.g., LPL).

The composition may further comprise an inhibitor of the endogenous lipase (e.g., LPL). The inhibitor may inhibit the lipase (e.g., LPL) from binding the recombinant protein. The inhibitor may inhibit the lipase from degrading the polysorbate.

The present invention also provides a method for producing a stable recombinant protein by the non-naturally occurring host cell of the present invention. The method comprises growing the non-naturally occurring host cell in a culture medium to produce a recombinant protein, and then making a composition comprising the recombinant protein and a polysorbate. The production of an endogenous lipase (e.g., LPL) by the host cell is reduced. The endogenous lipase (e.g., LPL) is capable of degrading the polysorbate, and is present in the composition in a small amount (e.g., less than about 10%, 5%, 1%, 0.1%, 0.01%, 0.001% or 0.0001% by weight). Preferably, the lipase is LPL.

The recombinant protein in the resulting composition is stable. For example, at least about 10%, 20%, 30%, 40%, 60%, 70%, 80%, 90% or 95%, preferably at least about 90%, more preferably at least about 95%, of the recombinant protein remains over a predetermined period of time, for example, about 1 day, 1 week, 2 weeks, 1 month, 3 months, 6 months or 1 year, preferably about 3 months.

According to the production method of the present invention, the recombinant protein may be a biopharmaceutical protein, for example, an antibody, preferably a monoclonal antibody, more preferably a humanized antibody. The antibody may be in the form of monomers, oligomers or large aggregates, preferably monomers. Exemplary recombinant proteins may include monoclonal antibodies (e.g., anti-EGFR mAb, anti-VEGF mAb, anti-Factor VIII mAb, anti-IgE mAb, anti-CD11a mAb, anti-interferon-β mAb, anti-TNFα mAb, anti-CD52mAb, anti-HER2mAb, and anti-CD20 mAb), human secreted alkaline phosphatase (SEAP), tissue plasminogen activator (tPA), α-glucosidase, laronidase, Ig-CTLA4 fusion, N-acetylgalactosamine-4-sulfatase, luteinizing hormone, erythropoietin, TNFα receptor fusion, Factor IX, follicle stimulating hormone, β-glucocerebrosidase, and deoxyribonuclease I. The recombinant proteins may have various targets and mechanisms of action, for example, Alpha4/beta1/7 integrin, Alpha-galactosidase ERT, ATIII substitution, B-lymphocyte stimulator (BLyS), CD20, Complement C5 antagonist, EGF-R, EpCAM (cancer target) and CD3 (T cell recruitment), Epitope on RS virus, Factor VIII substitution, G-CSF receptor, Glycoprotein IIb/IIIa antagonist, Growth hormone (GH) receptor antagonist, hGH receptor, Human gluco-cerebrosidase ERT, Iduronate-2-sulfatase enzyme replacement, IL-1 beta antagonist, IL-12 (p40) and IL-23, Insulin receptor, Insulin-like growth factor-1 (IGF-1) receptor agonist, Interferon alpha receptor, Interleukin-1 receptor (IL-1R) antagonist, Kallikrein, Keratinocyte growth factor receptor, Neuromus-cular transmission (SNAP-25 cleavage), Substitution of coagulation Factor VIIa, Thrombopoietin (TPO) receptor agonist, TNF alpha antagonist, TNF-alpha (soluble and membrane bound), and Vascular endothelial growth factor (VEGF). Where the recombinant protein has a biological activity (e.g., a therapeutic effect), at least about 10%, 20%, 30%, 40%, 60%, 70%, 80%, 90% or 95%, preferably at least about 90%, more preferably at least about 95%, of the biological activity remains over a prescribed period of time, for example, about 1 day, 1 week, 2 weeks, 1 month, 3 months, 6 months or 1 year, preferably about 3 months.

According to the production method of the present invention, the host cell produces at least about 10%, 20%, 30%, 40%, 60%, 70%, 80%, 90% or 95%, preferably at least about 20%, more preferably at least about 50%, less lipase (e.g., LPL) than a control cell. The control cell is the same as the host cell except that its endogenous lipase (e.g., LPL) production is not altered. The control cell may be a naturally occurring cell. Preferably, the host cell does not produce the lipase (e.g., LPL).

The production method may further comprise reducing the production of the endogenous lipase (e.g., LPL) by the host cell. For example, the production method may further comprise expressing an interfering RNA in the host cell or knocking out at least one copy, preferably all copies, of an endogenous gene encoding the endogenous lipase (e.g., LPL) from the genome of the host cell. The interfering RNA may be selected from the group consisting of small interfering RNAs (siRNAs), short hairpin RNAs (shRNAs), and bifunctional RNAs.

Where the host cell produces endogenous lipase (e.g., LPL), the produced endogenous lipase (e.g., LPL) may be bound to the recombinant protein. The endogenous lipase (e.g., LPL) bound to the recombinant protein may be removed from the recombinant protein by techniques known in the art. For example, the bound lipase (e.g., LPL) may be removed from the recombinant protein by washing, adding an excipient, or using an affinity column. The production method may further comprise removing the endogenous lipase (e.g., LPL) bound to the recombinant protein, either before or after making the composition comprising the recombinant protein and the polysorbate. In some embodiments, the percentage of the recombinant protein in the composition that is bound to the endogenous lipase (e.g., LPL) may be reduced by at least about 10%, 20%, 30%, 40%, 60%, 70%, 80%, 90% or 95%, preferably by at least about 20%, more preferably by at least about 50%, most preferably by at least about 95%. In a preferred embodiment, the recombinant protein in the composition is not bound to the endogenous lipase (e.g., LPL).

Where the composition comprises the endogenous lipase (e.g., LPL), the production method may further comprise removing the endogenous lipase (e.g., LPL) from the composition. The lipase (e.g., LPL) removal may be accomplished by techniques known in the art. For example, the endogenous lipase (e.g., LPL) may be removed from the composition by adding an excipient or using an affinity column. In some embodiments, the percentage of the endogenous lipase (e.g., LPL) in the composition is reduced by at least about 10%, 20%, 30%, 40%, 60%, 70%, 80%, 90% or 95%, preferably by at least about 20%, more preferably by at least about 50%, most preferably by at least about 95%. In a preferred embodiment, the resulting composition comprises no endogenous lipase (e.g., LPL).

The production method may further comprise adding an inhibitor of the endogenous lipase (e.g., LPL) to the composition. The inhibitor may inhibit the lipase (e.g., LPL) from binding the recombinant protein. The inhibitor may inhibit the lipase from degrading the polysorbate.

For each non-naturally occurring host cell suitable for producing a recombinant protein according to the present invention, a method for preparing the host cell is provided. The preparation method comprises reducing the production of endogenous lipase (e.g., LPL) by the host cell. Preferably, the lipase is LPL. The production of the endogenous lipase (e.g., LPL) may be reduced by at least about 10%, 20%, 30%, 40%, 60%, 70%, 80%, 90% or 95%, preferably by at least about 20%, more preferably by at least about 50%. In a preferred embodiment, the host cell does not produce the endogenous lipase (e.g., LPL). The host cell may be a mammalian cell selected from the group consisting of CHO, 3T3, BHK, HeLa, NS0, HepG2, and derivatives thereof. Preferably, the host cell is a CHO cell. The preparation method may further comprise expressing an interfering RNA specific for the lipase (e.g., LPL) in the host cell. The interfering RNA may be a small interfering RNA (siRNA), short hairpin RNA (shRNA), or bifunctional RNA. The interfering RNA may be encoded by the genome of the host cell. Alternatively, the preparation method may further comprise knocking out at least one copy, preferably all copies, of an endogenous gene encoding the endogenous lipase (e.g., LPL) from the genome of the host cell.

For each composition according to the present invention, a method for preparing the composition is provided. The preparation method comprises adding a polysorbate to a formulation comprising a recombinant protein produced by the non-naturally occurring host cell of the present invention. Preferably, the lipase is LPL. The production of endogenous lipase (e.g., LPL) by the host cell is reduced by, for example, at least about 10%, 20%, 30%, 40%, 60%, 70%, 80%, 90% or 95%, preferably by at least about 20%, more preferably by at least about 50%. The endogenous lipase (e.g., LPL) is present in the composition in a small amount (e.g., less than about 10%, 5%, 1%, 0.1%, 0.01%, 0.001% or 0.0001% by weight), and is capable of degrading the polysorbate. The recombinant protein is stable in the composition. For example, at least about 10%, 20%, 30%, 40%, 60%, 70%, 80%, 90% or 95%, preferably at least about 90%, more preferably at least about 95%, of the recombinant protein remains over a predetermined period of time, for example, about 1 day, 1 week, 2 weeks, 1 month, 3 months, 6 months or 1 year, preferably about 3 months. The recombinant protein may be an antibody, preferably a monoclonal antibody, more preferably a humanized antibody. Where the recombinant protein has a biological activity (e.g., a therapeutic effect), at least about 10%, 20%, 30%, 40%, 60%, 70%, 80%, 90% or 95%, preferably at least about 90%, more preferably at least about 95%, of the biological activity remains over a predetermined period of time, for example, about 1 day, 1 week, 2 weeks, 1 month, 3 months, 6 months or 1 year, preferably about 3 months. The polysorbate may be composed of one or more polyoxyethylene sorbitan monooleate fatty acid esters. For example, the polysorbate may comprise polysorbate 80, polysorbate 20, polysorbate 40, polysorbate 60, polysorbate 65, or a combination thereof. The production method may further comprise adding an inhibitor of the endogenous lipase (e.g., LPL) to the composition. The inhibitor may inhibit the lipase (e.g., LPL) from binding the recombinant protein. The inhibitor may inhibit the lipase from degrading the polysorbate.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1. Expression of Difficult-to-Remove Host Cell Protein Impurities During Extended Chinese Hamster Ovary Cell Culture and their Impact on Continuous Bioprocessing During biopharmaceutical manufacturing, Chinese hamster ovary (CHO) cells produce hundreds of extracellular host cell protein (HCP) impurities, which must be removed from the therapeutic product by downstream purification operations to ensure patient safety. A sub-set of 118 of these HCPs have been reported as exceptionally difficult to remove during downstream purification because they co-purify due to retention characteristics on chromatographic media and/or product-association through strongly attractive interactions to the therapeutic protein. As the biopharmaceutical industry moves towards continuous bioprocessing, it is important to consider the impact of extended culture of CHO cells on the expression of extracellular HCP impurities, especially those HCPs known to challenge downstream purification. Two complementary proteomic techniques, two-dimensional electrophoresis (2DE) and shotgun, were applied to detect variations in the extracellular CHO HCP profile over 500 days of culture. In total, 92 HCPs exhibited up to 48-fold changes in expression, with 34 of these HCPs previously reported as difficult to purify. Each proteomic technique detected differential expression by a distinct set of HCPs, with 10 proteins exhibiting significant variable expression by both methods. This study presents the impact of cell age on the extracellular CHO HCP impurity profile and identifies HCPs with variable expression levels, which warrant further investigation to facilitate their clearance in downstream purification.

1. Introduction

Typically, therapeutic proteins are secreted into the extracellular media along with hundreds of endogenous host cell protein (HCP) impurities, comprising both secreted proteins and intracellular proteins released during cell death. Purification processes clear these extracellular CHO HCPs from the therapeutic proteins because even low levels of HCP impurities have the potential to cause adverse patient reactions. A subset of these HCPs are difficult to remove during downstream purification because they exhibit product association with mAbs or similar retention to mAbs on chromatographic media. Variable expression during upstream cell culture, which changes the composition of the impurity profile fed into downstream purification, can increase the complexity of removing these difficult-to remove impurities because the composition of HCPs generated upstream has been shown to impact impurity clearance during downstream purification. HCPs with variable expression during cell culture in addition to co-purifying across purification are particularly likely to persist across purification operations into the final drug product. Consequently, it is necessary to identify specific HCPs that are likely to vary during cell culture and to characterize how these specific impurities are cleared in downstream operations.

Analysis of extracellular CHO HCPs can be achieved by proteomic techniques including two-dimensional electrophoresis (2DE) and shotgun methods, which are complementary techniques that can be applied to separate and quantify proteins and peptides, respectively. Proteomic techniques have been applied to track HCP clearance across various purification operations and to identify specific HCPs that are difficult to remove from therapeutic products during downstream purification. For example, HCPs likely to persist across capture by Protein A chromatography have been demonstrated by 2DE and shotgun methods, while HCPs likely to co-purify across alternative resin moieties have been identified by shotgun techniques. 2DE methods have also been applied to identify HCPs likely to evade clearance due to strongly attractive interactions with mAbs. In total, 118 HCP impurities have been reported as exceptionally difficult to purify during downstream purification in previous work. Variable expression of these difficult-to-remove HCPs during upstream operations may further challenge their clearance in downstream purification.

In the context of upstream biopharmaceutical manufacturing, input factors such as temperature and media composition have been shown to exhibit a limited effect on the extracellular CHO HCP impurity profile; however, extracellular HCP expression is significantly impacted by conditions that decrease cell viability. As manufacturing platforms evolve towards continuous bioprocessing, it is important to evaluate the impact of additional upstream factors on the HCP composition, particularly with regard to HCPs that are difficult to remove during downstream purification. Continuous bioprocessing represents an innovative technology characterized by integrating perfusion cell culture with continuous chromatography and other unit operations, and offers the potential for decreased cost and increased flexibility compared to traditional manufacturing platforms. Perfusion cultures have been demonstrated for over 60 days of continuous operation, during which the HCP profile may change through genetic modifications and phenotypic changes. Beckmann et al. applied 2DE to study the intracellular CHO proteome over 420 days of culture and demonstrated variable expression of several intracellular HCPs, including increased expression of several glycolytic enzymes and anti-stress proteins. Consequently, the composition of extracellular CHO HCP impurities requiring removal from a therapeutic product may evolve over extended cell culture during continuous bioprocessing and challenge removal during downstream operation. If purification operations are not designed to remove the full range of HCP levels resulting from such variable expression, product quality could be negatively impacted. Variable expression of HCPs that have been previously demonstrated as difficult to remove during downstream purification poses additional level of complexity for impurity clearance.

This study is the first to report changes in the extracellular CHO HCP composition associated with cell age upstream and to identify HCPs with variable expression that may impact impurity clearance during downstream processes, with a particular focus on HCPs that have been previously reported as difficult to remove during downstream purification. Cells cultured for four different durations of up to 500 days were compared by 2DE and shotgun proteomics. In total, 630 unique proteins were identified by the two techniques, with 92 extracellular CHO HCPs demonstrating variable expression relative to the shortest culture duration (136 days). Additionally, 37% of HCPs exhibiting varied expression in this work have previously been identified as potentially difficult to remove by downstream processes. These proteins represent a sub-set of the extracellular CHO proteome, which may be especially difficult to remove; further investigation of these HCPs could facilitate improved clearance in downstream purification.

2. Materials and Methods 2.1 Extended Culture of CHO Cells

A null CHO-K1 cell line (ATCC, Manassas, Va.) was adapted to serum-free, suspension culture in 125 mL shake flasks containing 20-30 mL SFM4CHO medium (Hyclone Laboratories Inc., Logan, Utah). The adaptation process occurred over 136 days, after which the cells were subjected to extended culture with routine passaging at 3-5 day intervals in a 37° C. cell culture incubator with 5% $CO_2$ and 80% relative humidity. At four time-points during culture (136, 251, 366, and 500 days), a portion of cells was removed and cryopreserved at $0.5-2.3 \times 10^6$ cells/mL in 7.5% dimethyl sulfoxide (Sigma-Aldrich Chemical Co., St. Louis, Mo.), 50% conditioned media, and 42.5% fresh media. These cryopreserved cell stocks from four different cell ages were stored using polypropylene cryogenic vials (Corning Inc., Corning, N.Y.) in liquid nitrogen until further use.

2.2 CHO Cell Production Cultures

The four cryopreserved cell stocks were thawed in parallel, transferred to 125 mL shake flasks containing 20 mL media, and cultured for 11 days until typical growth rates were regained. Cultures from each cell age were then seeded at $5 \times 10^4$ cells/mL and incubated with orbital agitation for 10 days in a 37° C. cell culture incubator with 5% $CO_2$ and 80% relative humidity. Cells were counted daily using a Fuchs Rosenthal hemocytometer (Hausser Scientific Co., Horsham, Pa.) with viability determined by the Trypan blue exclusion method. Portions of the extracellular CHO HCPs were harvested daily and separated from the residual cells by centrifugation (180 g, 10 min) and stored at −20° C. until further use. All samples were analyzed for total protein concentration by Bradford assay (Pierce Chemical, Rockford, Ill.). Four biological replicates of production culture sourced from a single cryopreserved stock were performed for each cell age Production culture replicates were performed from two separate experiments, each with an independent thaw of the cryopreserved stocks.

2.3 Quantitative Shotgun Proteomics

Samples containing 200 μg of extracellular CHO HCP harvested on day five of the production culture were precipitated with methanol by previously optimized methods (Valente et al., 2014, Biotechnol. J. 9:87-99) and resolubilized in 100 mM triethylammonium bicarbonate buffer (Sigma-Aldrich Chemical Co.). Residual detergent was removed by DetergentOUT™ GBS10-800 detergent removal kit (G-Biosciences, St. Louis, Mo.) according to the manufacturer's protocol. Triethylammonium bicarbonate buffer was removed by drying protein pellets in a Speed-Vac™ vacuum concentrator (Thermo Fisher Scientific Inc., Waltham, Mass.) and protein pellets were resolubilized in dissolution buffer with denaturant (both from iTRAQ™ reagent kit, AB Sciex, Framingham, Mass.). For each sample, 80 μg protein was reduced, alkylated, digested and labeled according to the manufacturer's protocol. HCPs from cells cultured for 136, 251, 366, and 500 days were labeled with iTRAQ™ tags (isobaric labels to quantify relative expression) 117, 116, 115, and 114, respectively. Protein concentration was measured by Bradford assay (Thermo Fisher Scientific Inc., Rockford, Ill.) both from the cell culture supernatant and following detergent removal.

Peptide separation by reversed phase high performance liquid chromatography (RPHPLC) was performed as described previously (Valente et al., 2014, Biotechnol. J. 9:87-99). Briefly, peptides were first separated by high-pH RP-HPLC on an Agilent 1100 (Agilent Technologies, Santa Clara, Calif.) using a 0.5 mL Varian PLRP-S column (Agilent Technologies). Elution was achieved by an acetonitrile gradient in 50 mM ammonium hydroxide (Avantor, Center Valley, Pa.), with eluate pooled into 15 fractions, which were further separated by low-pH RP-HPLC using a Tempo LCMALDI spotter (Eksigent, Dublin, Ireland) with a 1.2 μL CapRod RP-18E capillary column (Merck KGaA, Darmstadt, Germany). Peptides were eluted by an acetonitrile gradient in 0.1% trifluoroacetic acid (Avantor) and eluate was spotted onto target plates with α-cyano-4-hydroxycinnamic acid (Sigma-Aldrich Chemical Co.) matrix.

Data were collected by matrix-assisted laser desorption/ionization tandem time-of-flight (MALDI-TOF/TOF) mass spectrometry (MS) as described previously (Valente et al., 2014, Biotechnol. J. 9:87-99) on an AB Sciex 5800 MALDI-TOF/TOF Analyzer. Data were acquired in positive ion MS reflector mode and MS/MS with a maximum of 8 precursors per spot, and then submitted for database searches through ProteinPilot software v3.0 (AB Sciex). Spectra were searched against translations of the CHO genome (Xu et al., 2011, Nat. Biotechnol. 29:735-741) with cysteine alkylation by methyl methanethiosulfonate. Peptide identifications with 95% confidence or greater and protein identifications containing at least one significant (p≤0.05) unique peptide were accepted.

Relative protein quantitation and statistical analysis were performed through ProteinPilot software with automatic bias and background correction. Only peptides that were distinct to each protein were considered for relative quantitation. Proteins were defined as variably expressed if (1) they included at least four significant (p≤0.05) peptides, (2) they exhibited statistically significant differential expression (p≤0.01) at any cell age relative to expression in cells cultured for 136 days, and (3) they satisfied a 5% false discovery rate criterion (q≤0.05).

2.4 2DE Proteomics

2DE was performed as described previously (Valente et al., 2012, Electrophoresis 33:1947-1957) using 200 or 300 µg extracellular CHO HCP from each cell age with HCPs harvested on day five of the production culture and protein concentration measured from the cell culture supernatant by Bradford assay. HCPs were precipitated by tricholoracetic acid (Fisher Scientific, Fair Lawn, N.J.) according to previously optimized methods (Valente et al., 2014, Biotechnol J 9:87-99). Briefly, proteins were precipitated with 15% tricholoracetic acid, washed with acetone, and resolubilized in rehydration solution comprising 8 mM tris(hydroxymethyl)aminomethane (Bio-Rad Laboratories, Hercules, Calif.), 8 M urea (Bio-Rad Laboratories), 30 mM dithiothreitol (Bio-Rad Laboratories), 2% 3-[(3-cholamidopropyl)dimethylammonio]-1-propanesulfonate (Sigma-Aldrich Chemical Co.), 0.4% BioLytes (Bio-Rad Laboratories), and trace bromophenol blue (Bio-Rad Laboratories). Resolubilized proteins were used to rehydrate 18 cm, pH 3-10 nonlinear Immobiline DryStrips (GE Healthcare, Chalfont St. Giles, United Kingdom) and isoelectric focusing (IEF) was performed using a PROTEAN IEF Cell (Bio-Rad Laboratories) for 100,000 Vh, after which IEF gels were sequentially equilibrated with dithiothreitol and iodoacetamide (Sigma-Aldrich Chemical Co.). SDS-PAGE was performed using 13% T, 2.6% C polyacrylamide slab gels, which were stained with SYPRO Ruby (Molecular Probes, Eugene, Oreg.) and imaged on an FLA-3000 Fluorescent Image Analyzer (Fujifilm Corp., Tokyo, Japan). Gel images were analyzed and compared using ImageMaster 2D Platinum Software v5.0 (GE Healthcare). Spots were detected using the auto-detect feature and manually edited to remove artifacts, while spot matching was performed manually by comparing images. The relative spot volume was calculated by normalizing the volume of each protein spot to the total spot volume detected in each image. Spots exhibiting at least a three-fold change in relative volume across the four cell ages were excised for identification.

Excised spots were analyzed by MALDI-TOF/TOF MS as described previously (Valente et al., 2014, Biotechnol. J. 9:87-99) on an AB Sciex 4800 MALDI-TOF/TOF Analyzer. Data were acquired in positive ion MS reflector mode and MS/MS, and then submitted for Mascot v2.2 (Matrix Science Ltd., London, UK) database searches through GPS Explorer software v3.6 (AB Sciex). Spectra were searched against translations of the CHO genome and the NCBInr database with 50 ppm mass tolerance, and oxidation of methionines and carbamidomethylation of cysteines allowed as variable modifications. Identifications with 95% confidence or greater were accepted.

2DE analysis was performed on three biological replicates of production culture sourced from a single cryopreserved stock for each cell age. The relative spot volumes from spots with varied expression were tested for statistical significance by ANOVA using JMP Pro 10 (SAS Institute Inc., Cary, N.C.). Only protein spots that were detected on all three replicates of each cell age were considered, and multiple spots yielding identification of a single protein were collated prior to statistical analysis. Proteins identified were defined as variably expressed if they exhibited statistically significant differential expression (p≤0.1). For proteins with variable expression, relative protein expression was determined by normalizing the relative spot volume of each spot to the corresponding relative spot volume at day 136. The statistical significance of pairwise comparisons to cells cultured for 136 days was calculated by the Tukey-Kramer HSD test using JMP Pro 10.

3. Results 3.1 Cell Growth with Varied Cell Age

To streamline proteomic analysis without interference from an overexpressed product, CHO-K1 cells were used because null CHO cells have demonstrated equivalent HCP compositions to recombinant protein producing cell lines (Grzeskowiak et al., 2009, Protein Expr. Purif. 66:58-65; Jin et al., 2009, Biotechnol. Bioeng. 105:306-316; Tait et al., 2011, Biotechnol. Bioeng. 109:971-982). Cryopreserved stocks of CHO-K1 cells aged 136, 251, 366, and 500 days were cultured for 10 days, with daily analysis of viable cell density (FIG. 1A), cell viability (FIG. 1B), extracellular CHO HCP concentration (FIG. 1C), and extracellular CHO HCP productivity per cell (FIG. 1D). As these data were collected from null CHO cells, the HCP productivity per cell represented in FIG. 1D refers to the concentration of extracellular CHO HCPs normalized to the viable cell density over 10 days of production culture, and not the productivity of a recombinant product. Cells cultured for 136, 251, and 500 days all exhibit typical exponential growth over the first five days of culture and achieve a maximum cell density at day seven (FIG. 1A), followed by a decrease in cell density corresponding to a loss of cell viability (FIG. 1B). For these three cell ages, the growth rate and maximum cell density correlate with culture age, with older cells demonstrating increased growth. Conversely, cells cultured for 366 days show a different growth profile, attaining a maximum cell density after four days in culture, followed by a steady decrease in cell density over the remainder of the production culture (FIG. 1A). Statistically equivalent viability is observed across all cell ages for the first five days of culture, after which viability decreases with increasing cell age (FIG. 1B). Cells cultured for 366 days exhibit the greatest CHO HCP concentration (FIG. 1C), resulting in the greatest CHO HCP productivity (FIG. 1D).

3.2 Shotgun Proteomics

On day five of the production culture, supernatant from all four cell ages was collected for iTRAQ™ shotgun proteomics. In total, 3658 significant (p≤0.05) peptides were detected, resulting in identification of 630 unique HCPs, of which 85 HCPs (13%) demonstrated varied expression (p≤0.01, with q≤0.05) relative to expression in cells cultured for 136 days. Variable expression was observed in 47, 59, and 50 HCPs from cells cultured for 251, 366, and 500 days, respectively. 65% of HCPs with varied expression exhibited at least a three-fold change in expression level, with increases of up to 44-fold (atrial natriuretic factor) and decreases of up to 48-fold (complement C3) observed.

Of the 85 HCPs that exhibited variable expression by iTRAQ™ shotgun proteomics, 24 demonstrated expression that correlated with cell age (FIG. 2A). For example, laminin subunit beta-1 expression increased with cell age, while expression of chondroitin sulfate proteoglycan 4 decreased with cell age. Eight of the 24 proteins with cell age-dependent expression, such as lysosomal protective protein, exhibited a statistically significant decrease in protein expression for cell ages spanning 136 to 366 days, followed by a slight, significant increase in protein expression between 366 and 500 days (FIG. 2A, bottom panel). Additionally, 20 proteins showed expression that correlated with extracellular CHO HCP productivity (FIG. 2B), such as complement C3, which exhibits a positive correlation and 78 kDa glucose-regulated protein, which demonstrates a negative correlation. FIG. 3 shows the relative protein expression of laminin subunit α-5 (FIG. 3A) and complement C3 (FIG. 3A) as examples of cell age-dependent expression and productivity-dependent expression, respectively. The remaining 41 proteins with varied expression either demonstrated variable expression that did not correlate with cell age or productivity, exhibited maxima or minima in cells aged 251 or 500 days, or lacked enough statistically significant data to elucidate a correlation.

3.3 2DE Proteomics

Figure 6:
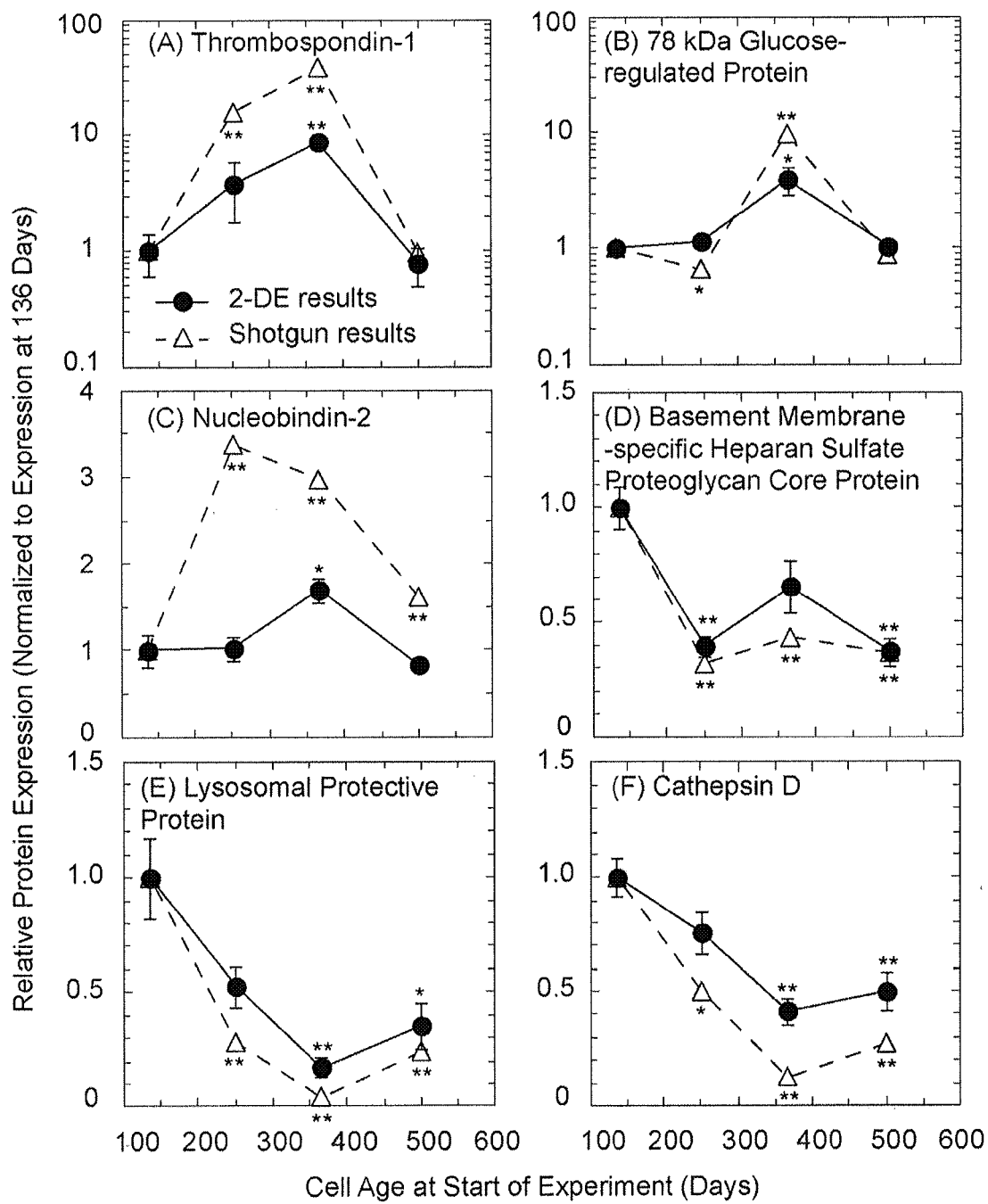
FIGS. 6A-F show relative protein expression by 2DE and shotgun proteomics for six proteins with the lowest p-value by 2DE: (A) thrombospondin-1, (B) 78 kDa glucose-regulated protein, (C) nucleobindin-2, (D) basement membrane-specific heparan sulfate proteoglycan core protein, (E) lysosomal protective protein, and (F) cathepsin D. Only protein spots exhibiting at least a threefold change in relative spot volume are included in relative protein expression by 2DE and multiple spots yielding the same protein identification were combined for each image. Error bars represent the standard error of the mean normalized spot volume from three biological replicates of production culture sourced from a single cryopreserved stock for each cell age. Statistical significance calculated by Tukey-Kramer HSD test with respect to expression at cells cultured 136 days and denoted as **p<0.01 and *p<0.05 for both proteomic methods.

Representative 2DE images of extracellular CHO HCPs harvested on day five of production culture are shown, with magnified images of select spots to illustrate variable expression, across cells cultured for 136 (FIG. 4A), 251 (FIG. 4B), 366 (FIG. 4C), and 500 (FIG. 4D) days. Across three biological replicates of production culture sourced from a single cryopreserved stock for each cell age, 50 protein spots exhibited at least a three-fold change in spot volume and were subsequently identified by MS. These 50 spots resulted in the identification of 32 unique proteins (FIG. 5, with identifications listed in Table 2), of which 17 demonstrated statistically significant variations in expression ($p<0.1$) by ANOVA, including seven HCPs that did not exhibit variable expression by shotgun proteomics (Table 2). The significance criterion applied to 2DE ($p<0.1$) was less stringent than that for shotgun ($p<0.01$) because the decreased number of ANOVA required for 2DE analysis (32 proteins compared to 631 for shotgun) reduces the absolute number of false positive identifications at a given confidence level. Relative HCP expression agrees between 2DE and shotgun methods for both the six proteins with the lowest p-values by 2DE (FIG. 6) and the remaining proteins with significant varied expression by 2DE. 2DE exhibits decreased magnitudes of change in relative HCP expression compared to shotgun proteomics, with a maximum increase of 6-fold exhibited by thrombospondin-1 and a maximum decrease of 9-fold demonstrated by lysosomal protective protein.

3.4 Difficult-to-Remove HCPs

From cells cultured for 251, 366, and 500 days, 92 unique HCPs exhibited variable expression relative to expression in cells cultured for 136 days by either shotgun (85 proteins) or 2DE (17 proteins) methods, with 10 proteins showing varied expression by both techniques. Of these 92 HCPs, 34 have previously been reported as potential purification challenges (Table 3). Seventeen of these HCPs are difficult to remove because they were shown to exhibit strongly attractive interactions with mAbs under Protein A solution conditions (Levy et al., 2014, Biotechnol. Bioeng. 111:904-912), while 15 of these HCPs were previously detected in Protein A eluate (Doneanu et al., 2012, MAbs 4:24-44; Hogwood et al., 2013, Biotechnol. Bioeng. 110:240-251). The remaining difficult-to-remove HCPs demonstrated similar retention characteristics to therapeutic products on a variety of polishing resins, including mixedmode, cation exchange, and multimodal chromatography (MMC) ligands (Joucla et al., 2013, J Chromatogr. B 942-943:126-133; Pezzini et al., 2011, J. Chromatogr. A 1218:8197-8208).

4. Discussion

The specific growth rate and maximum viable cell density increased with cell age for cells cultured for 136, 251, and 500 days, consistent with previous research. Conversely, cells cultured for 366 days achieved the lowest viable cell density and greatest extracellular CHO HCP concentration. Cells cultured for 366 days also exhibited the greatest HCP productivity, which can be attributed to enhanced HCP production and/or secretion rather than release of intracellular HCPs by cell lysis, because cells cultured for 366 and 500 days exhibit equivalent viability throughout the production culture. The unique cell growth demonstrated by cells cultured for 366 days is unexpected as culture conditions were consistent throughout the 500 days of culture and cells were not subjected to additional external stress at 366 days.

Because CHO cells are highly amenable to genetic modifications, the decreased cell growth exhibited by cells cultured for 366 days may result from random mutations resulting in unfavorable genomic changes between 251 and 366 days of culture. This hypothesis is supported by previous works that have documented the loss of specific productivity of a therapeutic product due to genetic instability, even in populations originating from a single CHO cell. Furthermore, it is reasonable that additional genetic mutations may have occurred between 366 and 500 days that either reversed the unfavorable mutations or induced additional mutations resulting in a phenotype with recovered cell density. As these results were determined from four biological replicates of production culture sourced from a single cryopreserved stock for each cell age, the reproducibility of CHO cell adaptation and extended cell culture remains unknown. Given the unique growth demonstrated by cells cultured for 366 days, it would be useful to replicate the entire process of CHO cell adaptation and extended culture to evaluate the reproducibility of the observed decrease in cell growth at 366 days of culture.

In total, 92 HCPs exhibited varied expression, with 92% detected by iTRAQ™ shotgun proteomics, 18% detected by 2DE, and 11% detected by both techniques. This finding is in agreement with previous work using the same complementary proteomic methods. For example, comparisons of HCT-116 cell lysates with varied p53 expression, *Escherichia coli* lysates with varied induction levels and times, and human lung squamous carcinoma versus normal tissue showed 85-97% of differentially expressed proteins were identified by iTRAQ™, 13-35% were identified by 2DE, and 4-29% were identified by both methods. Increased detection by shotgun proteomics compared to 2DE is reasonable because shotgun proteomics identifies peptides, while identification of proteins by 2DE is limited by reduced throughput and visual detection of spots during manual excision. For the 10 proteins identified by both methods in this work, relative expression trends were in agreement across techniques, with iTRAQ™ shotgun proteomics exhibiting an increased magnitude of expression change compared to 2DE, which is consistent with previous reports.

Because 2DE detects predominantly proteins and shotgun workflows detect peptides, identification of distinct groups of proteins by each technique is expected because the varied physicochemical properties of each protein result in different resolution between the two different methods. For example, 2DE is limited in detecting proteins with extreme hydrophobicity, molecular weight, or isoelectric point. Consequently, the majority (57%) of the seven proteins that exhibited varied expression by 2DE alone (Table 2) are cytoplasmic, while less than 7% of proteins identified as differentially expressed by shotgun proteomics are classified as cytoplasmic. Shotgun methods begin with a proteolytic digestion of proteins into peptides and are therefore limited in their ability to measure protein-level changes because a single peptide may originate from multiple proteins or protein isoforms, while multiple peptides derived from the same protein may show varied quantification due to the varied physicochemical properties of each peptide.

Differences between the precipitation methods required to maximize proteome coverage for each technique may also have contributed to the unique set of proteins detected by each method. For example, three of the HCPs only identified by 2DE (cofilin-1, glutathione transferase class pi, nucleoside diphosphate kinase B) are relatively small with molecular weight less than 25 kDa. One limitation of organic solvent precipitation, such as the methanol precipitation used to prepare HCPs for shotgun proteomics in this work, is decreased efficiency of recovery of small proteins, while the TCA precipitation used to prepare HCPs for 2DE is less dependent on protein size. Consequently, the seven HCPs that were not detected by shotgun proteomics may have exhibited better recovery during sample preparation for 2DE compared to shotgun analysis.

Three of the extracellular CHO HCPs identified in this study (cofilin-1, glutathione transferase, and peroxiredoxin-1) had previously been identified as being variably expressed within the intracellular proteome as a result of extended culture. As the present study examined the extracellular proteome from high-viability (>95%) cultures, it is expected that few proteins would overlap with those identified by Beckmann et al. given the substantial difference in HCP composition between intracellular and extracellular proteomes. The limited overlap between the two studies supports the hypothesis that the majority of HCPs identified in this work exhibit variable expression due to changes in expression or secretion rather than release of intracellular proteins by cell lysis.

Of the 92 HCPs with variable expression, a subset of 24 HCPs exhibited expression that correlated with cell age. Most of the proteins within this subset are classified as extracellular (71%) or lysosomal (21%) and serve functions related to cell adhesion, proteolysis and metabolism, and angiogenesis. Additionally, a subset of 21 proteins exhibited a productivity-dependent correlation, with most of these HCPs located extracellularly (48%) or in the endoplasmic reticulum (ER, 43%) and serving functions related to protein folding, proteolysis and metabolism, cell adhesion, and complement and immunity. Nine of the 20 productivity-correlated proteins demonstrated maximum expression in cells cultured for 366 days, when maximum HCP productivity was observed. One such protein, thrombospondin-1, inhibits cell growth as a tumor suppressor and therefore may contribute to the reduced viable cell density in cells cultured for 366 days. The majority (67%) of the nine proteins with expression positively correlated to HCP productivity are located in the ER. Increased expression of ER proteins may activate apoptosis and consequently contribute to the observed reduction in viable cell density in cells cultured for 366 days. The increased detection of ER proteins in the 366 day cultures likely results from increased production and/or secretion of these proteins and not increased cell lysis because expression of actin, a highly abundant intracellular HCP, did not exhibit statistically significant changes across the four cell ages (Table 2). This hypothesis is further supported by detection of equivalent amounts of L-lactate dehydrogenase A chain across all four cell ages, as lactate dehydrogenase is an intracellular protein that is commonly measured as a marker of cell health.

Of the 92 extracellular CHO HCPs exhibiting variable expression, 34 have previously been identified as difficult to remove due to co-elution and/or product association, and these proteins represent important candidates for additional exploration. For example, the majority (63%) of proteins previously identified as mAb-associating also show variable expression with cell age. Many of these proteins exhibited strong interactions with at least 3 different mAbs, including clusterin, chondroitin sulfate proteoglycan 4, G-protein coupled receptor 56, neural cell adhesion molecule, nidogen-1, lipoprotein lipase, and SPARC. Furthermore, approximately one-third of proteins previously shown to co-elute during capture by Protein A, mixed-mode, and cationic resins also exhibited variable expression with extended culture duration in this study. For example, 78 kDa glucose-regulated protein has previously demonstrated non-specific interactions with Protein A resin resulting in carry-over to Protein A eluate, and has been shown to co-elute with product fractions during purification by both mixed-mode and cationic resins. In this work 78 kDa glucose regulated protein exhibited variable expression by both proteomic techniques, including a productivity-dependent 10-fold expression increase by shotgun proteomics. Additionally, 6 HCPs (alpha-enolase, clusterin, cofilin-1, lysosomal protective protein, peroxiredoxin-1, and procollagen C endopeptidase enhancer 1) have been identified as purification challenges in at least three previous studies in addition to demonstrating variable expression in the present study. This list of proteins that may challenge purification by other mechanisms in addition to varied expression is not exhaustive because detection of the 92 proteins presented in this work may be problematic if the amount of protein expressed challenges the limit of detection of proteomic assays at certain culture durations.

5. Conclusions

Of the hundreds of extracellular CHO HCPs that must be cleared from therapeutic products, 118 have previously been reported as difficult to remove because they co-purify during downstream purification. This study shows that the composition of extracellular HCP impurities changes as CHO cells age, with variably expressed HCPs including a number of species that have previously been identified as difficult to remove. As biopharmaceutical manufacturing evolves towards continuous bioprocessing, it is important to consider the impact of extended cell culture on the HCP impurity profile because changes in expression of difficult-to-remove impurities may further challenge their clearance in downstream purification. To ensure product quality, purification operations must be designed to remove the full range of HCP levels resulting from such variable expression. Further investigation of extracellular CHO HCPs with variable expression, particularly those HCPs known to challenge downstream purification, could improve impurity clearance and enhance the robustness of manufacturing operations.

Example 2. Reduction of Lipoprotein Lipase by Small Interfering Ribonucleic Acids Limits Degradation of Polysorbate-80

1. Introduction

Polysorbates are a class of non-ionic surfactants that are often added to biopharmaceutical formulations to improve the stability of therapeutic proteins by limiting aggregation and surface adsorption. The majority of monoclonal antibody formulations incorporate polysorbate 80 (PS-80), which is composed of polyoxyethylene sorbitan monooleate fatty acid esters, to prolong the shelf-life of drug products.

The chemical structure of PS-80 is similar to that of a triglyceride, with both molecules containing long hydrocarbon chains attached by ester bonds. Degradation of PS-80 by hydrolysis of this ester bond can compromise the stability of therapeutic products.

Certain enzymes, such as lipoprotein lipase (LPL), hydrolyze ester bonds within triglycerides to form alcohol and fatty acid molecules. Given the structural similarities between PS-80 and triglycerides, it is hypothesized that LPL may enzymatically degrade PS-80. LPL is a host cell protein (HCP) that is expressed and secreted by Chinese hamster ovary (CHO) cells. Several factors indicate that LPL may be difficult to remove during biopharmaceutical manufacturing: it exhibits variable expression with cell age, it product-associates with different mAbs, and it demonstrates similar retention characteristics to mAbs during purification with three different polishing resins. Previous work has shown that recombinant CHO LPL produced in *Escherichia coli* degrades PS-80 at 37° C.

One method for limiting LPL content in biopharmaceutical drug products involves reducing LPL expression during upstream cell culture by silencing gene expression using short interfering ribonucleic acid (siRNA) technology. siRNAs are 21-23 nucleotide strands, with a sequence that is complementary to a specific target messenger RNA (mRNA). These siRNAs are incorporated into the RNA-induced silencing complex (RISC), which binds and cleaves the target mRNA sequence. mRNA cleavage inhibits translation and reduces expression of the target protein. The efficiency of siRNA-mediated gene silencing primarily depends on specific features of the siRNA sequence, including G/C content and strand stability. RNA interference has been demonstrated in CHO cells for bioprocess applications, such as improving recombinant productivity and extending culture duration. For example, siRNA-mediated silencing has been applied to reduce cofilin-1 expression, resulting in increased specific productivity, and to limit $\alpha$-1,6 fucosyltransferase expression and consequently generate defucosylated antibodies with improved antibody-dependent cellular cytotoxicity.

This research is the first study to apply siRNA technology to reduce expression of a difficult-to-remove HCP impurity, whose incomplete clearance may result in PS-80 degradation and reduced stability of biopharmaceutical products. Here, CHO cells are transfected with LPL-specific siRNAs to limit LPL expression, which is quantified by a multiple selected ion reaction monitoring (MRM) assay. Cell culture attributes are monitored to explore the impact of reduced LPL expression on cell growth, and the effect of LPL expression on PS-80 degradation is demonstrated.

2. Materials and Methods
2.1 CHO Cell Culture

A null CHO-K1 cell line (ATCC, Manassas, Va., USA) was adapted to serum-free, suspension culture in 125 mL shake flasks containing 20-30 mL SFM4CHO medium (Hyclone Laboratories Inc., Logan, Utah, USA). Following adaptation, the cells were subjected to extended culture with routine passaging at 3-5 day intervals in a 37° C. cell culture incubator with 5% CO2 and 80% relative humidity.

2.2 siRNA Design and Transfection

Adapted CHO cells were exchanged into Opti-MEM medium (Life Technologies, Carlsbad, Calif., USA) and independently transfected with three custom siRNAs (5'-GCAACAATGTGGGCTATGA-3' (SEQ ID NO: 11), 5'-CCTTTCTCCTGATGATGCA-3' (SEQ ID NO: 13), and 5'-GAAATGATGTGGCCAGGTT-3' (SEQ ID NO: 15)) and a non-specific control (all from Sigma-Aldrich Chemical Co., St. Louis, Mo., USA). Cells were transfected for 4-6 hours using Lipofectamine 2000 (Life Technologies) in 50 mL CultiFlask bioreactors (Sartorius Stedim Biotech, Gottingen, Germany), and subsequently diluted in SFM4CHO medium and cultured for 48 hours to enable siRNA-mediated silencing.

Following incubation, cells were counted using a Fuchs Rosenthal hemocytometer with viability determined by a Trypan blue exclusion method. The extracellular HCPs were harvested, separated from the residual cells by centrifugation (180 g, 10 min), analyzed for total protein concentration by Bradford assay (Pierce Chemical, Rockford, Ill., USA), and stored at −20° C. until further use.

2.3 Extracellular CHO HCP Preparation

HCPs were precipitated with methanol as described previously (Valente et al. 2014, Biotechnol. J. 9:87-99) and residual detergent was removed by DetergentOUT GBS10-800 detergent removal kit (G-Biosciences, St. Louis, Mo., USA) according to the manufacturer's protocol. Trypsin digestion was performed as described previously (Valente et al. 2014, Biotechnol. J. 9:87-99). Peptide pellets were resolubilized in 0.1% trifluoroacetic acid (TFA, Fisher Scientific, Fair Lawn, N.J., USA), loaded onto C18 ZipTips (EMD Millipore, Billerica, Mass., USA) and eluted in 50% acetonitrile with 0.1% TFA (Fisher Scientific).

2.4 MRM Assay

High pH reversed phase high performance liquid chromatography (RP-HPLC) was performed using an UltiMate 3000 nLC system (Dionex, Sunnyvale, Calif., USA). Digested CHO HCPs were loaded onto a C18 trap column (Dionex) and washed with 150 µL of 2% acetonitrile (Mallinckrodt Chemicals, Phillipsburg, N.J., USA) in 0.1% formic acid (Pierce Chemical). Peptides were eluted onto a 0.66 µL C18 column (Dionex) by a 26 column linear gradient from 2-49% acetonitrile, followed by an additional 6 column volumes of 49% acetonitrile. All operations were performed at 2.6 min residence time and both mobile phases included 0.1% formic acid. Column eluate was directly injected into a QTrap 4000 (AB Sciex, Foster City, Calif., USA) through a nanoSpray II source (ABSciex) with an uncoated fused-silica Pico tip (New Objective, Woburn, Mass., USA). The instrument was operated in positive ESI ion mode, with spray voltage of 2400 V and source temperature of 150° C., with MRM triggered enhanced resolution scan and enhanced product ion scans. Database searches were performed using ProteinPilot software v4.0 (ABSciex) against translations of the CHO genome. Possible MRM transitions were generated with Skyline v2.5.0.6157 and monitored through Analyst 1.6.2 (AB Sciex), with parameters specified in Table 4. Raw MRM data were integrated for peak area and normalized to yeast alcohol dehydrogenase (YAD) transition peak areas. All analysis was performed with three technical replicates and two biological replicates.

2.5 PS-80 Degradation Assay

Extracellular CHO HCPs prepared from siRNA transfected cells and control cultures were independently buffer-exchanged into pH 6.8 with 10 mM $CaCl_2$ (Sigma-Aldrich Chemical Co). PS-80 (Fisher Scientific) was then added to the buffer-exchanged HCPs to a final concentration of 23 mM (3% w/w) and the mixture was incubated at 37° C. for 24 hours with mixing. Enzymatic degradation of PS-80 was measured using the EnzyChrom Free Fatty Acid Kit (Fisher Scientific), which measures the concentration of fatty acid released during PS-80 hydrolysis.

3. Results and Discussion

Figure 7:
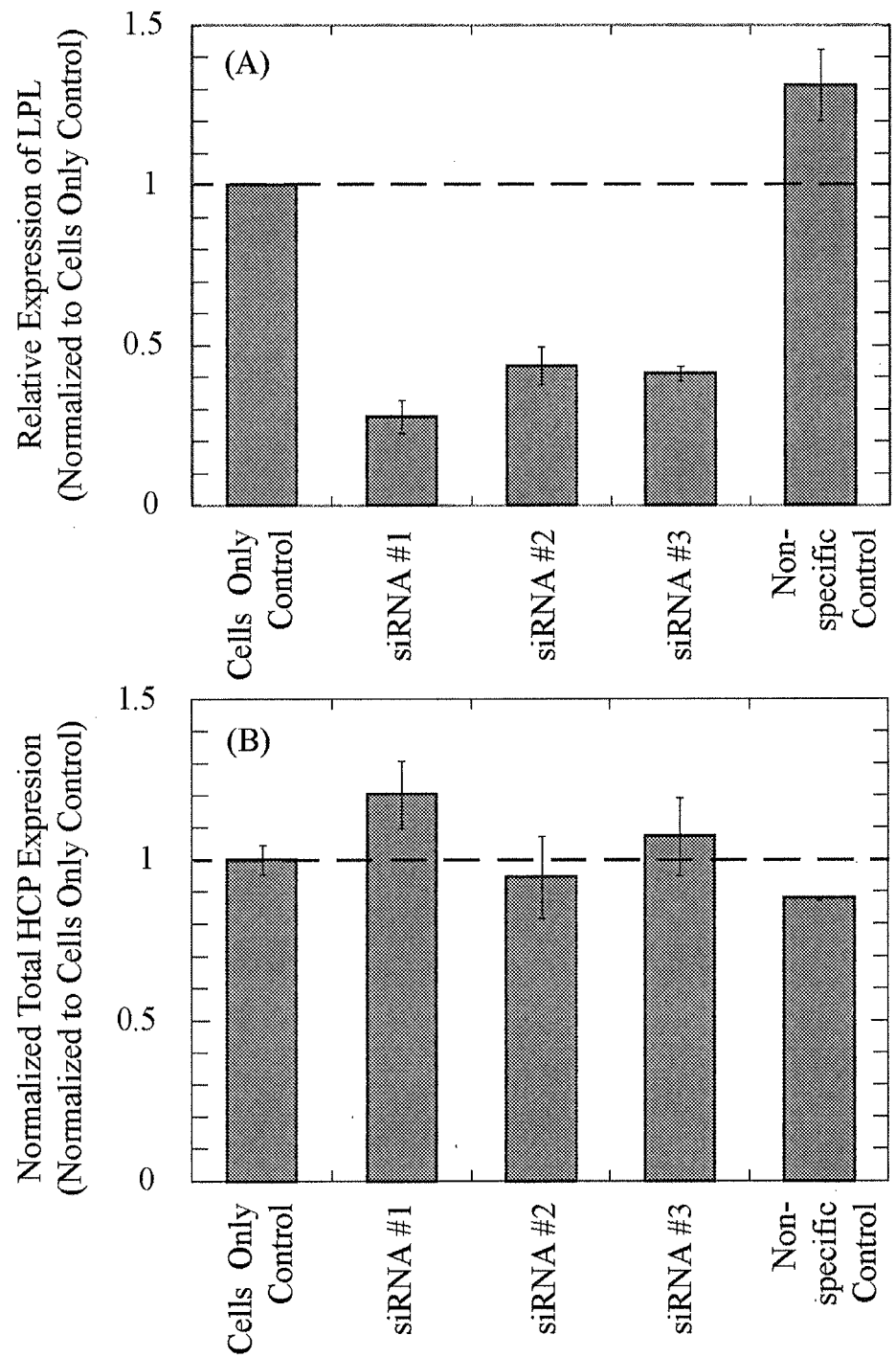
FIG. 7A-B show the impact of siRNA-mediated silencing on (A) LPL expression and (B) total HCP expression. Error bars represent the standard error of the mean from two biological replicates. LPL expression was also measured in technical triplicate (n=6 total measurements).
Figure 8:
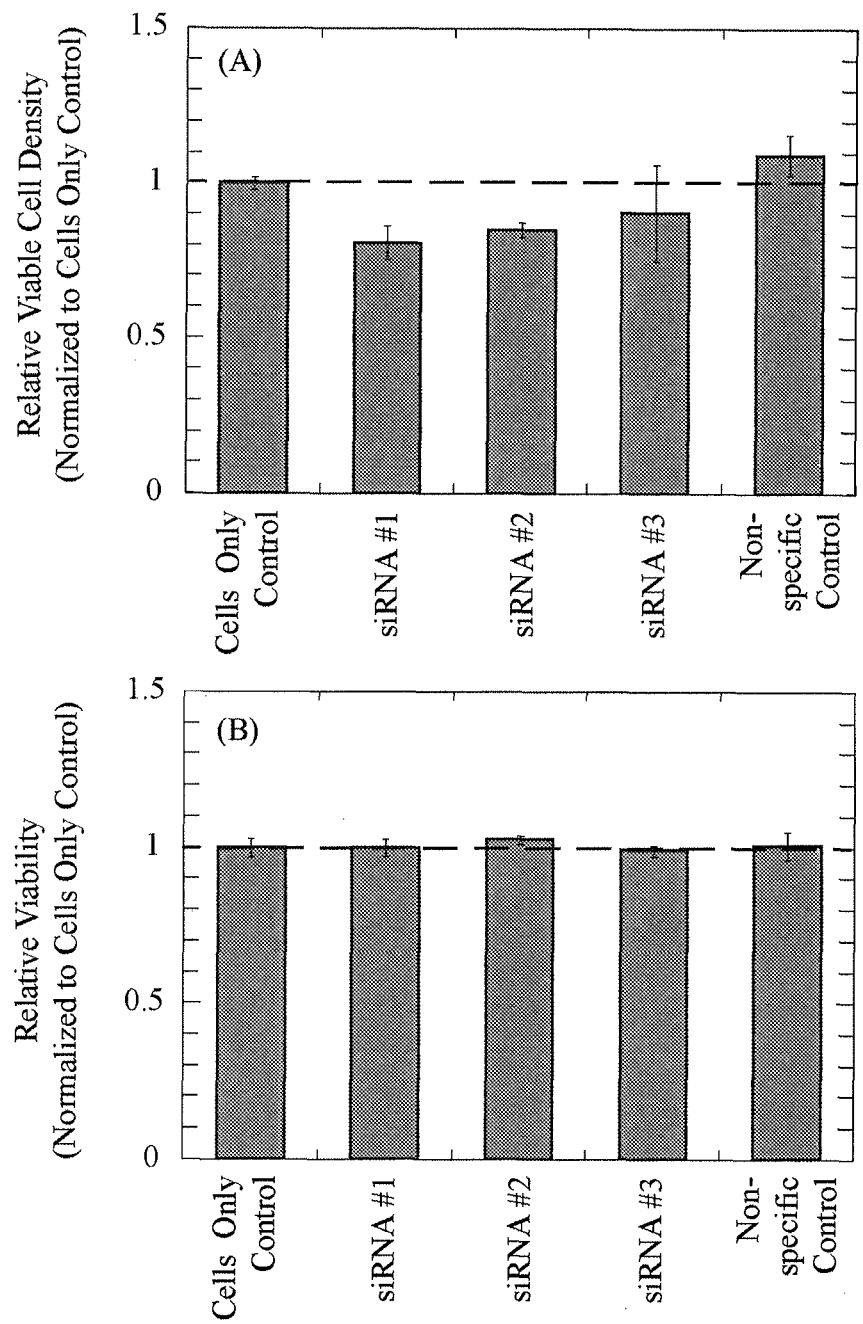
FIGS. 8A-B show cell culture performance with siRNA-mediated silencing of LPL. Measured cell culture attributes include (A) cell density and (B) cell viability. Error bars represent the standard error of the mean from two biological replicates.

CHO cells were transfected with three different siRNA sequences that are specific for different regions of the LPL gene as well as a non-specific control siRNA, and results were compared to those for untransfected CHO cells. The extracellular CHO HCPs were analyzed by a MRM assay to determine the relative amount of LPL in each culture. Transfection with LPL-specific siRNA reduced expression of LPL by 56-72% (FIG. 7A), while the total HCP expression remained similar across all five cultures (FIG. 7B). This reduction in LPL expression had a limited impact on cell growth, with LPL-specific siRNAs demonstrating a 10-19% reduction in average cell density (FIG. 8A) and equivalent viability exhibited by all cultures (FIG. 8B). The observed reduction in cell growth (FIG. 8A) following siRNA transfection is in agreement with previous reports using cofilin-specific siRNA (Hammond and Lee 2011, Biotechnol. Bioeng. 109:528-535) and α-1,6 fucosyltransferase-specific siRNA (Mori et al. 2004, Biotechnol. Bioeng. 88:901-908); however, transfection with a non-specific control previously demonstrated a reduced growth rate that was not observed in this study (Hammond and Lee 2011, Biotechnol. Bioeng. 109:528-535). Transfection with LPL-specific siRNAs reduced expression of the target HCP while maintaining other attributes that are relevant to biopharmaceutical manufacturing, demonstrating that this technique is suitable for evaluating difficult-to-remove HCPs. As transfection with siRNAs that are specific for three unrelated protein targets all resulted in decreased cell growth, this technology is best suited for applications that can tolerate a slight decrease in cell density.

Figure 9:
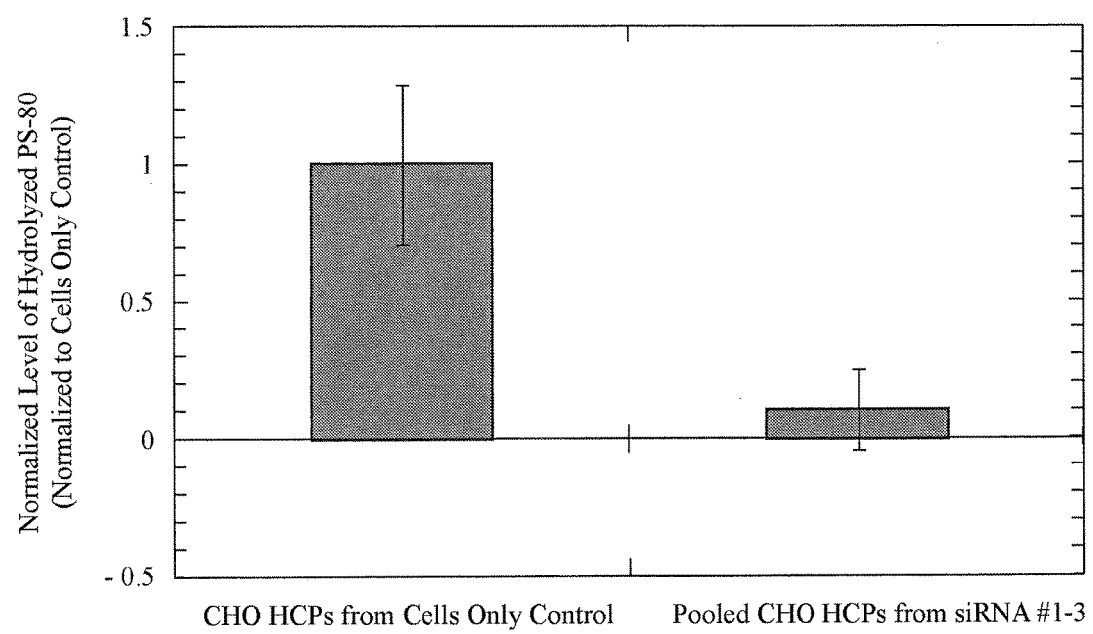
FIG. 9 shows PS-80 digestion following incubation with extracellular CHO HCPs derived from control culture and following siRNA-mediated silencing of LPL. Control cultures digested an average of 0.2% of the initial PS-80 concentration prior to normalization. Error bars represent the standard error of the mean from technical triplicate measurements.

The amount of PS-80 degradation can be determined by monitoring the formation of fatty acids in solution because PS-80 hydrolysis results in the release of free fatty acids. The extracellular CHO HCP pool from control cells degraded an average of 0.2% of the initial amount of PS-80, while the siRNA-transfected cultures with reduced LPL expression exhibit a level of PS-80 hydrolysis that is statistically insignificant (FIG. 9). Although low, the amount of PS-80 digestion by the control culture was significantly greater than the assay limit of quantitation (0.1%), suggesting that endogenous CHO LPL is capable of digesting PS-80. This finding is supported by previous reports that PS-80 is hydrolyzed by pancreatin, which contains a mixture of enzymes, including lipases (Christiansen et al., 2010, Eur. J. Pharm. Sci. 41:376-382). While the exact composition of HCPs from each CHO culture is unknown, the insignificant hydrolysis of PS-80 observed by the HCPs from cultures transfected with LPL-specific siRNA is consistent with LPL functioning as the primary extracellular CHO HCP responsible for PS-80 degradation.

4. Concluding Remarks

LPL is an HCP impurity that is expressed and secreted by CHO cells and difficult to remove during downstream purification operations because it exhibits product association and similar retention characteristics to mAbs on polishing chromatographic resins. The biological function of LPL is to hydrolyze ester bonds on triglycerides, which are structurally similar to PS-80, a surfactant that is added to most biopharmaceutical formulations to improve stability of the therapeutic product. This research shows that persistence of LPL through downstream purification operations and into the final drug product can degrade PS-80 and that reducing the expression of LPL in upstream cell culture operations can limit this degradation. The siRNAs used in this work can be applied to study LPL during biopharmaceutical process development or to reduce LPL expression during therapeutic protein manufacturing. Additionally, the siRNA-mediated silencing technique shown here is not specific to LPL and can be applied to study the impact of reduced expression of any difficult-to-remove HCP impurity.

Example 3. PS-80 Digestion by CHO Lipoprotein Lipase from CHO HCP Samples

Samples from CHO HCP were collected from CHO cells, from CHO cells expressing each of three different siRNA molecules designed to reduce LPL expression, and from CHO cells expressing a nonspecific siRNA molecule. The amount of PS-80 degraded was monitored using a fatty acid assay. Pefabloc, an enzyme inhibitor, was added to one sample to determine whether an inhibitor may block LPL activity and therefore impact PS-80 degradation. In FIG. 10A, the amount of PS-80 degraded by a sample containing no inhibitor is compared to a sample containing Pefabloc inhibitor. The sample without inhibitor demonstrates about 18 micromoles of PS-80 degradation compared to the sample with inhibitor which demonstrates 8 micromoles of PS-80 degradation. In FIG. 10B, the amount of PS-80 degradation performed by samples derived from siRNA-expressing CHO cells is compared to control cells. The control cells and CHO cells expressing a non-specific siRNA that would not be expected to significantly reduce PS-80 degradation show about 32 and 42 micromoles of PS-80 degraded. Some of the siRNA-expression cells (namely, the siRNA1 and siRNA2 cells) show somewhat less PS-80 degradation (28 and 23 micromoles of PS-80 degraded) in this experiment.

Example 4. Digestion of Polysorbate by CHO Lipoprotein Lipase Expressed in *E. coli*

1. Introduction

Polysorbates are nonionic surfactants that are common additives in therapeutic mAb formulations. Of the 30 FDA approved mAbs as of 2012, 19 contained polysorbate 80 and 4 contained polysorbate 20. Polysorbates protect mAbs from degradation during purification, filtration, freeze-drying, storage and final delivery. They are thought to stabilize high-concentration mAb solutions by binding to the product molecules or competing with mAbs for surface adsorption. Polysorbate degradation has previously been studied and several different routes of polysorbate degradation in formulations have been identified. Polysorbate degradation can lead to accelerated product degradation due to increased aggregation or oxidation due to peroxide formation.

Lipoprotein lipase (LPL) was identified as a difficult-to-remove HCP impurity in mAb downstream processing. The objectives of the present work are to determine if CHO LPL can enzymatically degrade polysorbates in the pH range of interest for typical mAb formulations (~pH 5-7).

2. LPL production

CHO LPL was expressed in *E. coli*, purified and refolded. Bacterial expression was used to produce large amounts of LPL rapidly.

2.1 Expression in *E. coli*

An LPL-containing pET11a plasmid was transformed into BL21-competent cells in SOC broth and plated on ampicillin. Colonies were selected and cultures were grown overnight to seed the production culture.

Figure 11:
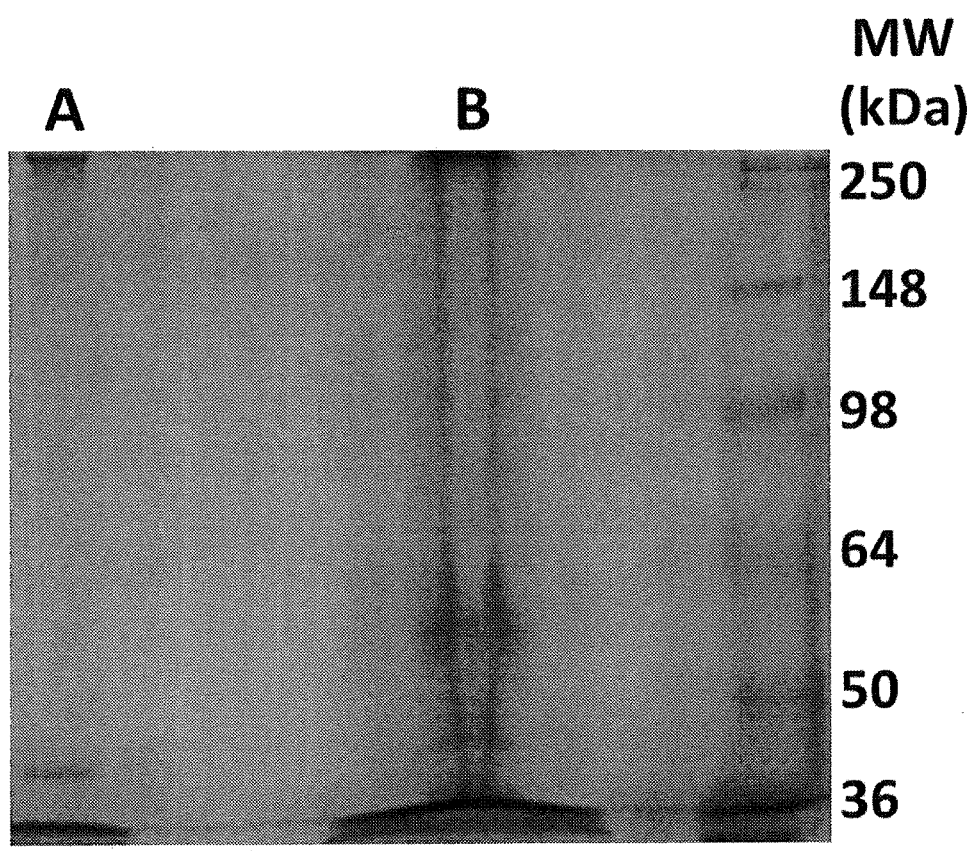
FIG. 11 shows silver-stained reducing SDS-PAGE of non-induced (A) and induced (B) LPL-producing E. coli cell cultures.

To confirm LPL protein expression, two cultures were run in autoclaved 25 mg/mL LB broth with 100 µg/mL ampicillin at 37° C. The cultures were run with and without isopropyl β-D-1-thiogalactopyranoside (IPTG) induction. Cells were then pelleted, redissolved in PBS and heated to 100° C. after the addition of SDS loading buffer. The material was loaded and run on a 10% SDS PAGE gel to confirm the expression of CHO LPL. The silver-stained gel is shown in FIG. 11. The culture with IPTG induction has a band not present in the non-induced culture at slightly greater than 50 kDa, which is consistent with LPL.

2.2 CHO LPL Purification

Figure 12:
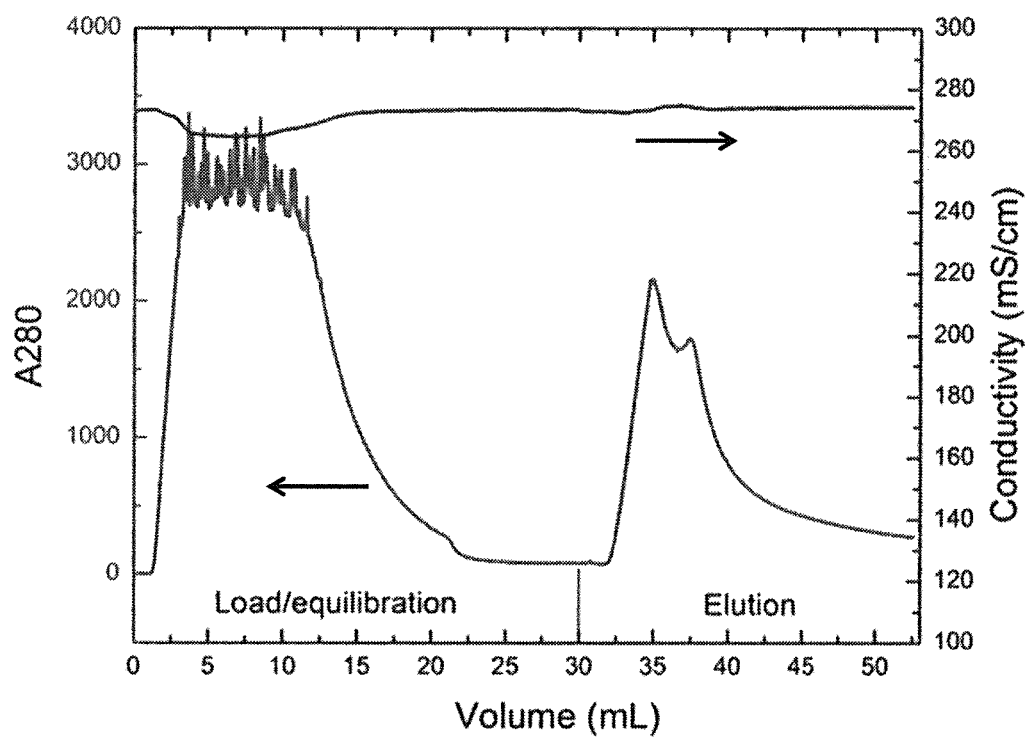
FIG. 12 shows Ni-NTA affinity purification of recombinant CHO LPL with 250 mM imidazole step elution.

After confirmation of LPL expression (FIG. 11), Ni-NTA affinity purification of LPL was completed. A 750 mL cell culture harvest was homogenized and LPL inclusion bodies were resolubilized in 6 M guanidine HCl. The resulting chromatogram of Ni-NTA affinity purification is shown in FIG. 12. The large A280 signal during loading is due to *E. coli* HCP impurities, cell debris and cell culture media additives flowing through the column. The step elution using 250 mM imidazole results in a large peak of eluting LPL with a pronounced tail. Throughout the Ni-NTA purification the mobile phase was maintained at 6 M guanidine HCl.

Figure 13:
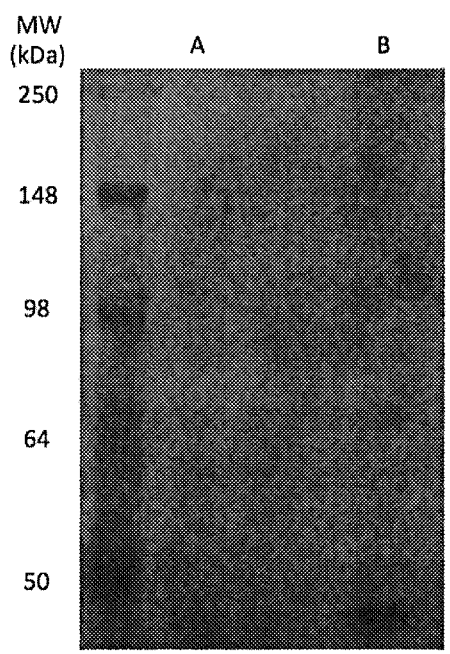
FIG. 13A-B show (A) the flow-through fraction A and elution fraction B of LPL Ni-NTA affinity purification on silver-stained reducing SDS-PAGE, and (B) anti-His western blot of the LPL Ni-NTA affinity purification flow-through fraction (A) and elution fraction (B).

SDS-PAGE was used to assess the purity of the Ni-NTA LPL elution pool. Samples were buffer-exchanged into PBS prior to loading the gel. The silver-stained reducing gel is shown in FIG. 13A. This gel indicates a single band in both lanes A and B at approximately 50 kDa. The elution pool (lane B) contains no detectable impurities. The flow-through pool has a diffuse band at the same molecular weight as the band in the eluate. A western blot was run to confirm the presence of His-tagged LPL and is shown in FIG. 13B. A mouse monoclonal anti-His tag antibody (G020, ABM, Richmond, BC, Canada) was used to detect His-tagged LPL. The anti-His western confirms that the ~50 kDa bands in the Ni-NTA flow-through and elution have a His-tag. The presence of LPL in the Ni-NTA flow-through is likely due to overloading the column. CHO LPL concentration was then determined using a Micro BCA™ assay (Thermo Scientific, Rockford, Ill.).

After confirming purification, LPL refolding was carried out by rapid dilution with gentle stirring; this method was the most successful of those explored and resulted in only limited precipitate formation.

Figure 14:
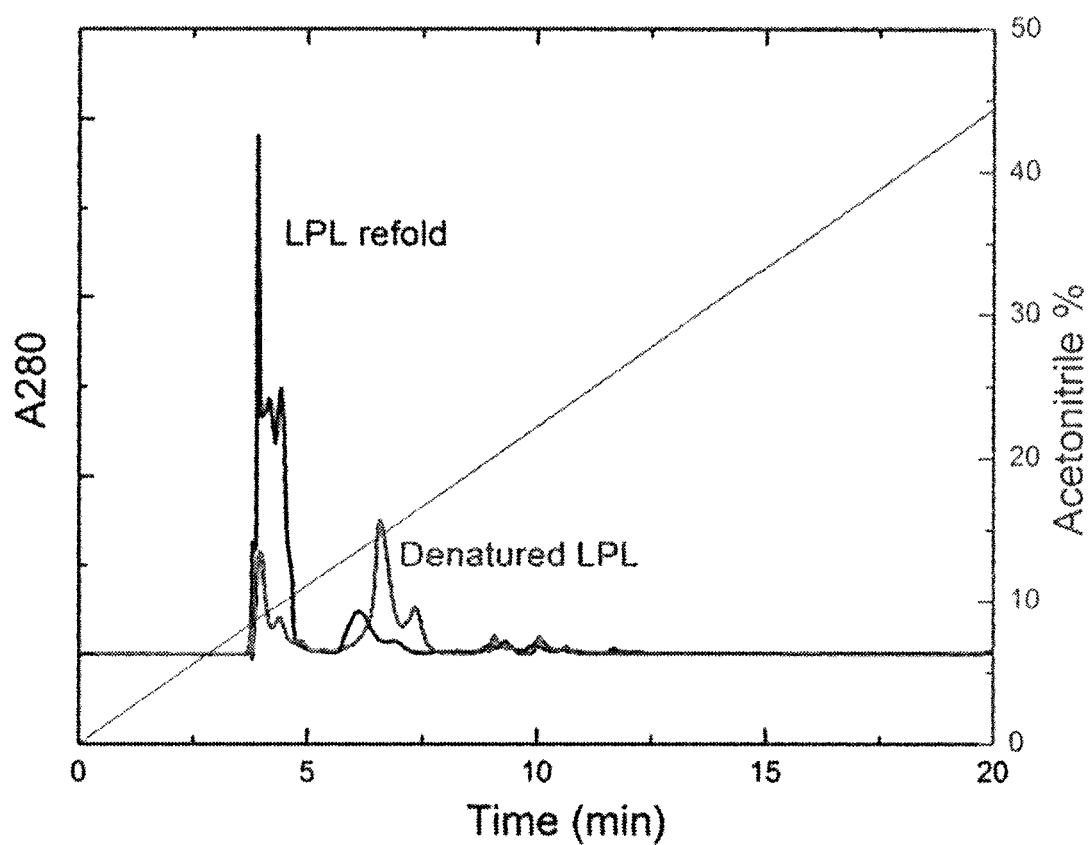
FIG. 14 shows RP-HPLC gradient elution (45 min 0-100% acetonitrile linear gradient, $C_{18}$ column, 1 mL/min) of refolded LPL (black) and LPL solubilized in 6 M guanidine HCl (gray).

To confirm folding, reverse phase (RP)-HPLC was run with unfolded LPL (LPL solubilized in 6 M guanidine HCl) and refolded LPL. The LPL was injected into the $C_{18}$ column at 1 mL/min with a linear gradient from 0-100% acetonitrile in water over 45 minutes. The chromatograms are shown in FIG. 14. The solubilized LPL has two main peaks and many smaller late-eluting peaks. The refolded LPL also has two main peaks. The majority of refolded LPL is contained in the early-eluting peak, likely due to less solvent exposure of the LPL hydrophobic core. The unfolded LPL interacts with the $C_{18}$ column with higher affinity, indicating that it has more hydrophobic character than the folded LPL. Unfortunately there is no CHO LPL standard to confirm correct folding. Without a proper standard this result cannot confirm proper LPL folding, but it does provide insight into the changes in LPL due to the refolding procedure. The enzymatic activity that was measured in subsequent sections is further evidence of proper folding of at least a subpopulation of the LPL.

3. Enzymatic Activity of CHO LPL Expressed in *E. coli*

Measurements of LPL activity against polysorbate 20 and polysorbate 80 were carried out in various solution conditions. Refolded LPL was buffer-exchanged into the appropriate buffer prior to the activity assay. The conditions investigated were pH 5.0, pH 6.0 and pH 6.8 and the buffers used were 10 mM sodium acetate, pH 5.0, 10 mM L-histidine, pH 6.0, and 50 mM bis-tris, pH 6.8. Polysorbate 20 or 80 was added to the buffer-exchanged LPL with a final concentration of 0.23 mM (0.03%). Some samples also had either 10 mM calcium chloride or 10 mM sodium chloride. The polysorbate and LPL solutions were then incubated at 37° C. with constant mixing for 24 hours.

To assay polysorbate degradation, 270 µM 9-anthryldiazomethane (ADAM) in methanol was added to each sample in a 3:1 ratio of ADAM solution to sample. The ADAM conjugation was carried out at room temperature using opaque 1.6 mL Eppendorf tubes with constant mixing for at least 6 hours. Following conjugation the samples were centrifuged at 13,000 g for 6 minutes and the supernatant was added to HPLC sample vials. A Viva C18 150×4.6 mm column from Restek (Bellefonte, Pa.) was used with a Shimadzu Prominence UFLC (Kyoto, Japan). The mobile phase was 97% acetonitrile, 3% methanol. Samples were all run in triplicate on the HPLC with injection volumes of 10 µL and a flow rate of 1 mL/min for 13 minutes per sample. The absorbance at 254 nm was analyzed for the characteristics peaks of degraded polysorbate 20, 80 or triglyceride. The EnzyChrom™ Free Fatty Acid Kit was used as a secondary method to confirm the results of the HPLC assay described by directly measuring the release of fatty acid by lipase.

4. Results and Discussion

Figure 15:
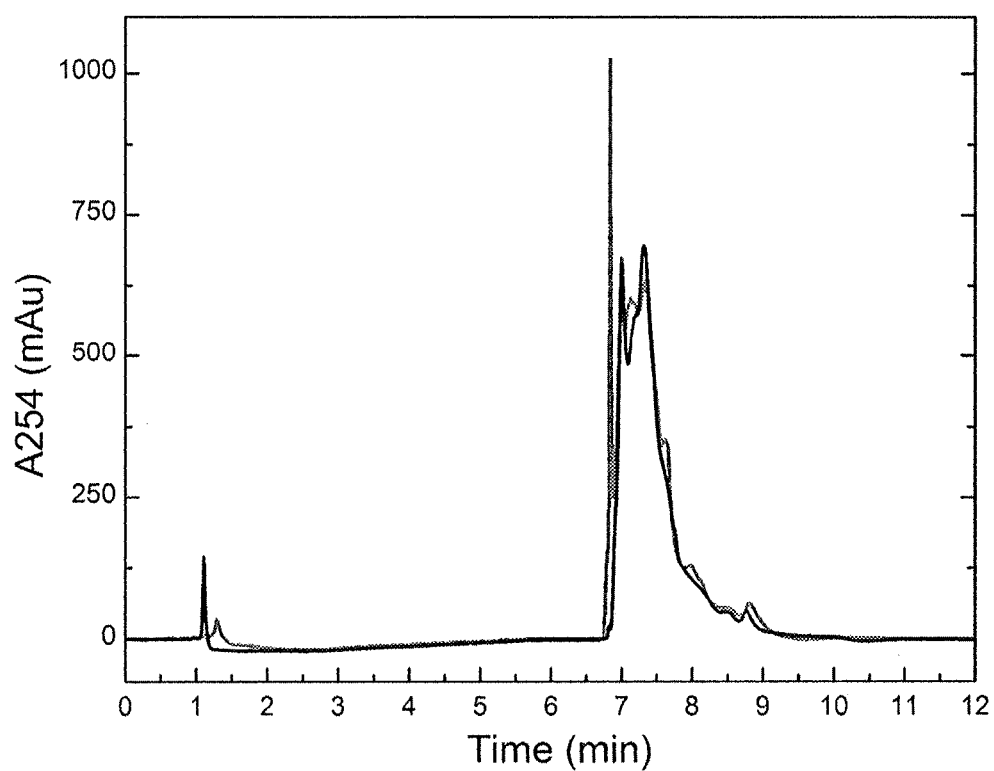
FIG. 15 shows representative chromatogram of ADAM-labeled degraded and non-degraded polysorbate 80.

For the ADAM labeling-HPLC assay, a sample chromatogram comparing degraded and non-degraded polysorbate 80 is shown in FIG. 15. The ADAM-labeled polysorbate degradation product has a characteristic peak at 7 minutes. Activity was measured at pH 5.0, 6.0 and 6.8 in the presence of either NaCl, $CaCl_2$ or no additional salt. These conditions were chosen as they are similar to FDA-approved mAb formulation conditions and $Ca^{2+}$ was previously found to promote the formation of active LPL dimers.

Figure 16:
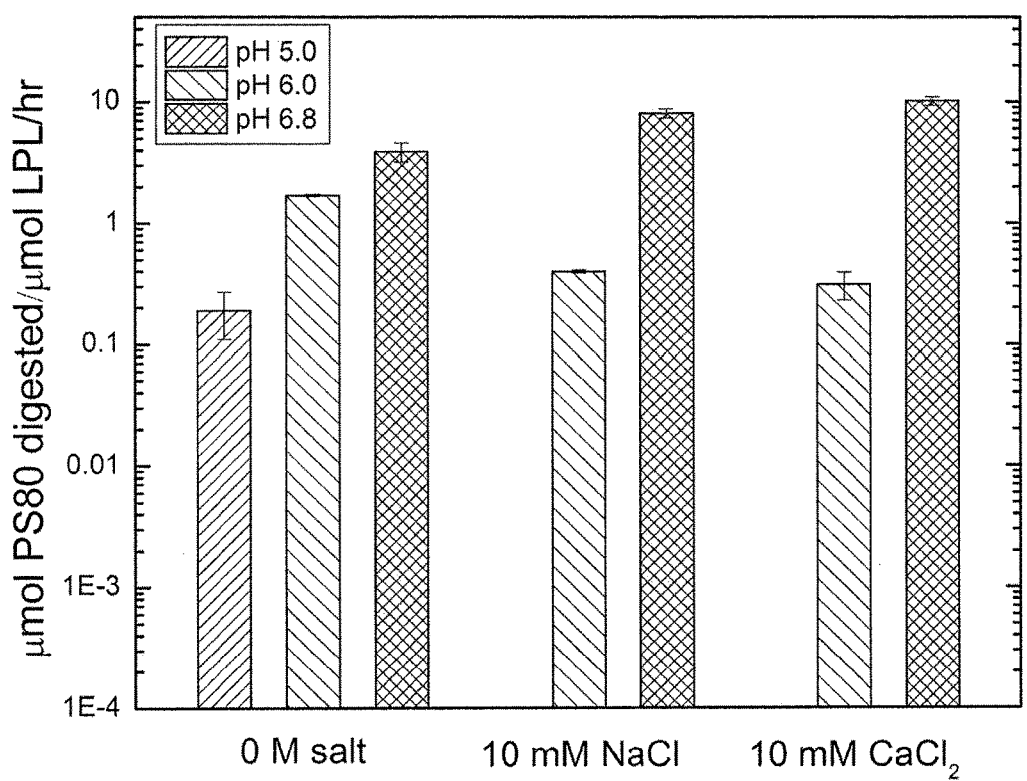
FIG. 16 shows digestion rate of polysorbate 80 by CHO LPL (produced in E. coli) in different solution conditions at 37° C. for 24 hours.

The experimentally measured degradation rates of polysorbate 80 are shown in FIG. 16. Overall, there is measurable polysorbate 80 degradation in almost all of the conditions tested. Although these degradation rates were measured at an unrealistically high temperature for mAb storage, it is helpful to put the measured rates into context. For example, in a formulation containing 10 ppm LPL, a degradation rate of 0.1 µM polysorbate/µM LPL/hr translates to a polysorbate degradation corresponding to concentrations of approximately 0.02-0.03% per year, so annual degradation amounts are comparable to the total polysorbate content in formulated samples. Degradation rates were found to increase with increasing pH, consistent with prior work on lipase catalysis that showed maximum rates at higher pH. The addition of the two salts has a minimal effect, contrary to previous findings. The most extensive degradation was found at pH 6.8 with 10 mM $CaCl_2$, but similar rates were found with NaCl and no additional salt, so neither salt appears necessary for active LPL against polysorbate 80. The degradation rates measured here were similar to previous findings with pancreatin.

Figure 17:
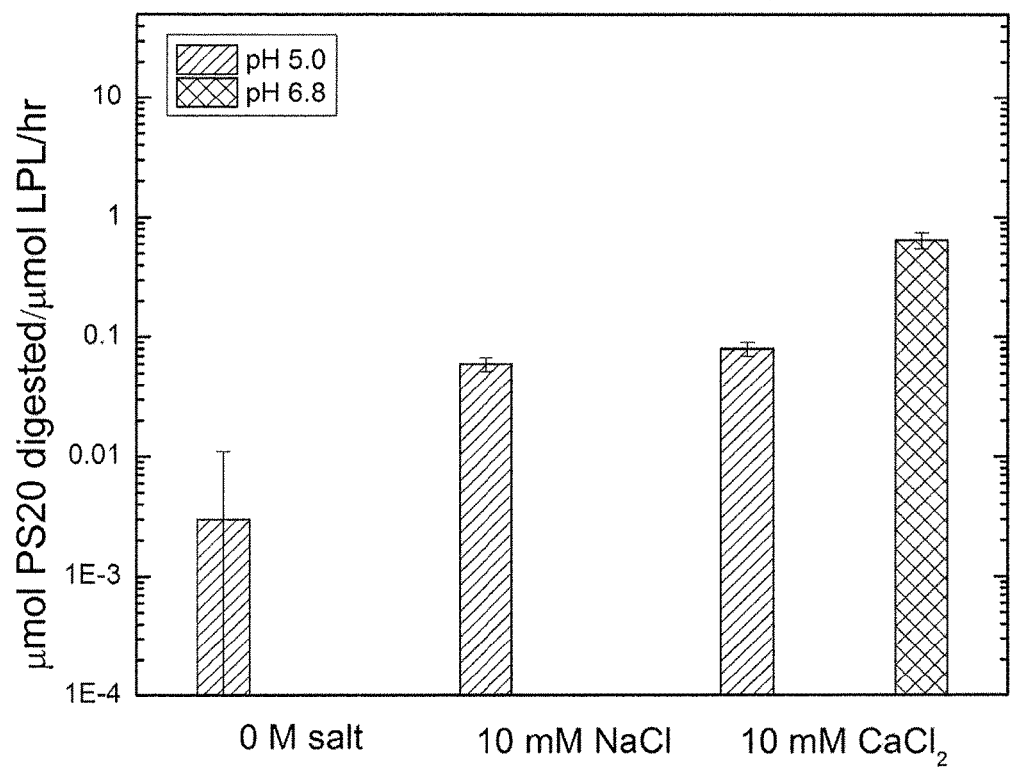
FIG. 17 shows digestion rate of polysorbate 20 by CHO LPL (produced in E. coli) in different solution conditions at 37° C. for 24 hours. No measurable digestion was found at pH 6.0.

LPL degradation rates of polysorbate 20 are shown in FIG. 17 for the same conditions as for polysorbate 80. Overall, LPL activity is much lower using polysorbate 20, which is less frequently added to formulations, but still commonly used. In contrast to the polysorbate 80 degradation results, most of the conditions with measurable degradation were at pH 5.0; polysorbate 20 at pH 6.8 with 10 mM $CaCl_2$ was the only other condition where degradation was detected. Polysorbate 20 degradation rates at pH 5.0 increase significantly upon the addition of either NaCl or $CaCl_2$, consistent with observations in previous work.

These findings demonstrate the possibility of polysorbate degradation due to CHO LPL presence in final formulations. HCPs with enzymatic activity have previously been observed to result in mAb degradation. The measured degradation rates show relative trends among different conditions, but the implications of the nominal rates in a bioprocessing environment cannot readily be interpreted meaningfully due to a number of significant differences. In particular, the *E. coli*-produced LPL lacks glycosylation and is probably not completely folded. Also, these studies were completed at an elevated temperature. Rates of LPL degradation of polysorbate at typical storage temperatures were not measured.

5. Conclusions

The polysorbate degradation studies reported here confirm that CHO LPL recombinantly produced in *E. coli* or natively produced by CHO cells can degrade either polysorbate 20 or 80 by ester hydrolysis in mAb formulation conditions. The optimal solution conditions for degradation of polysorbate 80 were consistent with previous findings for lipases. It was also found that for polysorbate 20, LPL had higher activity at pH 5.0 with either NaCl or $CaCl_2$ present at 10 mM.

These results demonstrate both the difficulty of removing LPL during mAb purification processes as well as the danger of not removing LPL. Degradation of polysorbate in formulations is a previously identified problem that should be avoided at all costs. At the very least LPL should be monitored through downstream purification and in final formulations; tracking LPL is not overly difficult and could provide insight into otherwise unexplained product degradation.

Example 5. Genome Editing of Host Cells

There are several approaches available to knock out the presence of specific target genes in a genome. So-called genome editing tools employ the CRISPR-Cas9 mechanism of gene editing, the use of TALENs or the use of zinc finger nucleases. We are studying the use of the CRISPR-Cas9 and also TALEN based approaches to knock out the presence of lipoprotein lipase from the genome of CHO cells. Because lipoprotein lipase is not believed to be an essential gene or protein, the knock out of this gene should allow cells to remain viable. Moreover, it will prevent expression of this particular host cell protein which is known to be difficult to remove. By eliminating expression of this gene, the protein cannot be expressed and it cannot coelute or copurify with recombinant proteins of interest. Because it will not be present in the purified recombinant protein, it will not be able to degraded polysorbates such as PS-80.

1. Transfection of hCas9+sgRNA and LPL-TALEN Plasmids in Suspension Serum-Free CHO Cells For CRISPI-Cas9 knock out, four different sgRNA target molecules are being tested for their ability to target and eliminate LPL from the CHO genome while not having any significant off target effects. In addition, a non-specific sgRNA molecule is also being tested as a control.

CRISPR transfection: $1\times10^6$ Suspension serum-free CHO cells were transfected with 1 µg hCas9 and 1 µg sgRNA plasmids using Lipofectamine 2000, according to manufacturer's protocol. Cells were incubated at 37° C. for 3 days.

| Experiment | Plasmids |
|---|---|
| 1 | 2 µg Cas9 only |
| 2 | Cas9, sgRNA_1 |
| 3 | Cas9, sgRNA_2 |
| 4 | Cas9, sgRNA_3 |
| 5 | Cas9, sgRNA_4 |
| 6 | Cas9, sgRNA_non-specific |

TALEN Transfection:

$1\times10^6$ suspension serum-free CHO cells were transfected with 1 µg LPL-TAL left and 1 µg LPL-TAL right plasmids using Lipofectamine 2000, according to manufacturer's protocol. Cells were incubated at 37° C. for 3 days.

2. Selection of Cells by Exposure to Selection Reagents 3 days after transfection, $0.5\times10^6$ CRISPR-transfected cells were exposed to 600 µg/mL Geneticin and 600 µg/mL Zeocin for 2 days. Genomic extraction was performed with the remaining cells using Qiagen's DNeasy Blood & Tissue Kit.

Cells were counted 2 days after exposure to selection reagents. However, 0% viability were seen in all CRISPR-transfected cells. Cells may be more vulnerable to the toxicity of the selection reagent after transfection. To determine the optimal concentration of selection reagents, tests with concentrations of selection reagents after transfection is needed.

3. Serial Dilution and Semi-Solid Media Plating of Transfected Cells 5 days after transfection, TALEN-transfected cells were serially diluted on a 96-well plate at a density of 0.5 cell/well. Cells were also plated in triplicates at 400 cells/mL in semi-solid media, supplemented with 4 mM L-glutamine, on 6-well plates. These plates will incubate at 37° C. for 10 days.

TABLE 1

LPL siRNA sequences

| Sense/Antisense | siRNA Design | Start | Target Sequence |
|---|---|---|---|
| Sense | GCAACAAUGUGGGCU AUGAdTdT (SEQ ID NO: 1) | 926 | GCAACAATGTGGGCT ATGA (SEQ ID NO: 11) |
| Antisense | UCAUAGCCCACAUUG UUGCdTdT (SEQ ID NO: 2) | 926 | TCATAGCCCACATTG TTGC (SEQ ID NO: 12) |
| Sense | CCUUUCUCCUGAUGA UGCAdTdT (SEQ ID NO: 3) | 588 | CCTTTCTCCTGATGA TGCA (SEQ ID NO: 13) |
| Antisense | UGCAUCAUCAGGAGA AAGGdTdT (SEQ ID NO: 4) | 588 | TGCATCATCAGGAGA AAGG (SEQ ID NO: 14) |
| Sense | GAAAUGAUGUGGCCA GGUUdTdT (SEQ ID NO: 5) | 392 | GAAATGATGTGGCCA GGTT (SEQ ID NO: 15) |
| Antisense | AACCUGGCCACAUCA UUUCdTdT (SEQ ID NO: 6) | 392 | AACCTGGCCACATCA TTTC (SEQ ID NO: 16) |
| Sense | CUUUGUCAUCGAGAA GAUUdTdT (SEQ ID NO: 7) | 1272 | CTTTGTCATCGAGAA GATT (SEQ ID NO: 17) |
| Antisense | AAUCUUCUCGAUGAC AAAGdTdT (SEQ ID NO: 8) | 1272 | AATCTTCTCGATGAC AAAG (SEQ ID NO: 18) |
| Sense | GAAGUAUUGGGAUCC AGAAdTdT (SEQ ID NO: 9) | 653 | GAAGTATTGGGATCC AGAA (SEQ ID NO: 19) |
| Antisense | UUCUGGAUCCCAAUA CUUCdTdT (SEQ ID NO: 10) | 653 | TTCTGGATCCCAATA CTTC (SEQ ID NO: 20) |

TABLE 2

Proteins with variable expression, which were identified by MS from 2DE images. Statistical significance determined by ANOVA of relative protein spot volume from three biological replicates of production culture sourced from a single cryopreserved stock for each cell age. Protein identifications from translations of the CHO genome unless otherwise noted.

| Spot # | Accession # | Protein Name | p-value |
| --- | --- | --- | --- |
| 1 | gi\|344252604 | Laminin subunit gamma-1 | 0.277 |
| 2 | gi\|344244798 | Nidogen-1 | 0.032 |
| 3 | gi\|304510 | 78 kDa glucose-regulated protein | 0.013 |
| 4 | gi\|344242104 | Sulfated glycoprotein 1 | 0.145 |
| 5 | gi\|344246008 | Lysyl oxidase-like 1 | 0.018 |
| 6 | gi\|16508150 | ERP57 protein | 0.013 |
| 7 | gi\|344250216 | Procollagen C-endopeptidase enhancer 1 | 0.016 |
| 8 | gi\|145567052 | Serine protease | 0.060 |
| 9 | gi\|115497814 | Nucleobindin-1 | 0.212 |
| 10 | gi\|344241583 | Lysosomal protective protein | 0.004 |
| 11 | gi\|344259113 | Pigment epithelium-derived factor | 0.126 |
| 12 | gi\|344251524 | Nucleobindin-2 | 0.008 |
| 13 | gi\|344248735 | Cathepsin D | 0.003 |
| 14 | gi\|761724 | Beta-actin | 0.429 |
| 15 | gi\|344254255 | Cathepsin B | 0.188 |
| 16 | gi\|344240379 | Vesicular integral-membrane protein VIP36 | 0.950 |
| 17 | gi\|344253656 | 3-phosphoinositide-dependent protein kinase 1 | 0.922 |
| 18 | gi\|344249681 | Clusterin | 0.706 |
| 19 | gi\|344242456 | Complement C1r-A subcomponent | 0.053 |
| 20 | gi\|344242993 | Collagen alpha-1(III) chain | 0.095 |
| 21 | gi\|344242455 | Calcium-dependent serine proteinase | 0.177 |
| 22 | gi\|344258664 | Metalloproteinase inhibitor 1 | 0.153 |
| 23 | gi\|344255270 | V-type proton ATPase subunit S1 | 0.102 |
| 24 | gi\|899229b | Thrombospondin-1 | 0.002 |
| 25 | gi\|7434045 | Glutathione transferase class pi | 0.023 |
| 26 | gi\|81917543 | Peroxiredoxin-1 | 0.078 |
| 27 | gi\|62948096 | Basement membrane-specific heparan sulfate proteoglycan core protein | 0.002 |
| 28 | gi\|344237299 | Immunoglobulin superfamily member 8 | 0.352 |
| 29 | gi\|344238428 | Peptidyl-prolyl cis-trans isomerase C | 0.294 |
| 30 | gi\|344256956 | Cofilin-1 | 0.045 |
| 31 | gi\|344252163 | Nucleoside diphosphate kinase B | 0.028 |
| 32 | gi\|344252164 | Nucleoside diphosphate kinase A | 0.683 |

TABLE 3

CHO HCPs previously identified as purification challenges by other mechanisms in addition to demonstrating varied expression with prolonged cultivation duration in this study.

| Protein Name | Product Assoc. | Protein A | Mixed-mode | Cation or MMC |
| --- | --- | --- | --- | --- |
| 78 kDa glucose-regulated protein | | x | x | x |
| Acid ceramidase | | | | x |
| Alpha-enolase | x | x | x | x |
| Basement membrane-specific heparan sulfate proteoglycan core protein | | | x | |
| Beta 2-microglobulin | | | x | x |
| Cathepsin D | x | | | x |
| Cathepsin Z | | | x | x |
| Chondroitin sulfate proteoglycan 4 | x | | | |
| Clusterin | x | x | | x |
| Cofilin-1 | | x | x | x |
| Collagen alpha-1(III) chain | | | x | |
| Complement C1r-A subcomponent | x | | | |
| Galectin-3-binding protein | x | | | |
| Glutathione transferase class pi | | | x | x |
| G-protein coupled receptor 56 | x | | | |
| Heat shock protein HSP 90-beta | | x | | |
| Insulin-like growth factor-binding protein 4 | | x | | |
| Laminin subunit alpha-5 | | x | | |
| Laminin subunit beta-1 | | x | | x |
| Laminin subunit gamma-1 | | x | | |
| Legumain | | | | x |
| Lipoprotein lipase | x | x | | |
| Lysosomal alpha-glucosidase | | x | | |
| Lysosomal protective protein | x | | x | x |

TABLE 3-continued

CHO HCPs previously identified as purification challenges by other mechanisms in addition to demonstrating varied expression with prolonged cultivation duration in this study.

| Protein Name | Product Assoc. | Protein A | Mixed-mode | Cation or MMC |
|---|---|---|---|---|
| Metalloproteinase inhibitor 1 | x | | | x |
| N(4)-(beta-N-acetylglucosaminyl)-L-asparaginase | | | | x |
| Neural cell adhesion molecule 1 | x | | | |
| Nidogen-1 | x | x | | |
| Peptidyl-prolyl cis-trans isomerase B | | | x | |
| Peroxiredoxin-1 | x | x | | x |
| Procollagen C-endopeptidase enhancer 1 | | x | x | x |
| Putative phospholipase B-like 2 | | | | x |
| Serine protease | | x | x | |
| SPARC | x | | | |

TABLE 4

MRM assay parameters.

| | Target peptide sequence | SEQ ID | Precursor (m/z) | Product (m/z) | Product ion | Scan time (ms) | CE (V) |
|---|---|---|---|---|---|---|---|
| LPL | ITGLDPAGPNFEYAEAPSR | 21 | 1002.987 | 793.424 | y72+ | 20 | 72.9 |
| | ITGLDPAGPNFEYAEAPSR | 21 | 1002.987 | 430.271 | y42+ | 20 | 67.9 |
| | ITGLDPAGPNFEYAEAPSR | 21 | 1002.987 | 359.204 | y32+ | 20 | 52.9 |
| | EPDSNVIVVDWLYR | 22 | 852.933 | 1162.662 | y92+ | 20 | 44.4 |
| | EPDSNVIVVDWLYR | 22 | 852.933 | 1063.594 | y82+ | 20 | 44.4 |
| | EPDSNVIVVDWLYR | 22 | 852.933 | 950.509 | y72+ | 20 | 44.4 |
| | ITGLDPAGPNFEYAEAPSR | 21 | 668.994 | 793.424 | y73+ | 20 | 37.8 |
| | ITGLDPAGPNFEYAEAPSR | 21 | 668.994 | 630.331 | y63+ | 20 | 37.8 |
| | ITGLDPAGPNFEYAEAPSR | 21 | 668.994 | 430.241 | y43+ | 20 | 37.8 |
| | LSPDDADFVDVLHTFTR | 23 | 974.476 | 661.352 | y52+ | 20 | 56.3 |
| | GLGDVDQLVK | 24 | 522.29 | 873.478 | y82+ | 20 | 30.5 |
| | GLGDVDQLVK | 24 | 522.29 | 701.429 | y62+ | 20 | 30.5 |
| | GLGDVDQLVK | 24 | 522.29 | 602.361 | y52+ | 20 | 30.5 |
| YAD | ANELLINVK | 25 | 507.3031 | 699.4763 | y62+ | 20 | 32.9 |
| | ANELLINVK | 25 | 507.3031 | 586.3923 | y52+ | 20 | 32.9 |
| | ANGTTVLVGMPAGAK | 26 | 693.8741 | 730.3916 | y82+ | 20 | 42.8 |
| | ANGTTVLVGMPAGAK | 26 | 693.8741 | 631.3232 | y72+ | 20 | 42.8 |
| | EALDFFAR | 27 | 484.7454 | 655.3198 | y52+ | 20 | 31.7 |
| | EALDFFAR | 27 | 484.7454 | 540.2929 | y42+ | 20 | 31.7 |
| | VVGLSTLPEIYEK | 28 | 483.2729 | 778.3981 | y63+ | 20 | 32 |
| | VVGLSTLPEIYEK | 28 | 483.2729 | 552.3028 | y43+ | 20 | 32 |

TABLE 5

Candidate protein A wash solutions adapted from previous work (Shukla and Hinckley, 2008).

| Wash number | pH | Wash contents |
|---|---|---|
| 1 | 4.4 | 50 mM citrate, 1% polysorbate 80 |
| 2 | 4.4 | 50 mM citrate, 1M urea |
| 3 | 9.0 | 25 mM tris, 10% isopropyl alcohol, 3M urea |
| 4 | 9.0 | 25 mM tris, 1% polysorbate 80, 10% isopropyl alcohol, 3M urea |

What is claimed:

1. A non-naturally occurring host cell comprising a nucleic acid sequence encoding recombinant protein, wherein the host cell expresses the recombinant protein, wherein the host cell expresses an interfering RNA specific for an endogenous lipoprotein lipase, whereby the production of the endogenous lipoprotein lipase by the host cell is reduced.

2. The non-naturally occurring host cell of claim 1, wherein the host cell is a mammalian cell selected from the group consisting of CHO, 3T3, BHK, HeLa, HepG2, and derivatives thereof.

3. The non-naturally occurring host cell of claim 1, wherein the interfering RNA is selected from the group consisting of small interfering RNAs (siRNAs), short hairpin RNAs (shRNAs), and bifunctional RNAs.

4. The non-naturally occurring host cell of claim 1, wherein the interfering RNA is encoded by the genome of the host cell.

* * * * *